US011559225B1

(12) United States Patent
Lee et al.

(10) Patent No.: US 11,559,225 B1
(45) Date of Patent: Jan. 24, 2023

(54) WEARABLE BIOFLUID VOLUME AND COMPOSITION MEASUREMENT SYSTEM

(71) Applicant: Epicore Biosystems, Inc., Cambridge, MA (US)

(72) Inventors: Stephen P. Lee, Ann Arbor, MI (US); Adam Leech, Lake Orion, MI (US); Weihua Li, Acton, MA (US); Alan P. Scarth, Boston, MA (US); Jeffrey B. Model, Cambridge, MA (US); Roozbeh Ghaffari, Cambridge, MA (US); Alexander J. Aranyosi, Somerville, MA (US); Melissa Seib, Somerville, MA (US); Jessica Wallace, Cambridge, MA (US)

(73) Assignee: Epicore Biosystems, Inc., Cambridge, MA (US)

( * ) Notice: Subject to any disclaimer, the term of this patent is extended or adjusted under 35 U.S.C. 154(b) by 0 days.

(21) Appl. No.: 17/746,407

(22) Filed: May 17, 2022

Related U.S. Application Data

(60) Provisional application No. 63/295,136, filed on Dec. 30, 2021.

(51) Int. Cl.
*A61B 5/145* (2006.01)
*A61B 5/00* (2006.01)
(Continued)

(52) U.S. Cl.
CPC .......... *A61B 5/14517* (2013.01); *A61B 5/002* (2013.01); *A61B 5/0022* (2013.01);
(Continued)

(58) Field of Classification Search
CPC ... A61B 5/14517; A61B 5/002; A61B 5/0022; A61B 5/01; A61B 5/1118;
(Continued)

(56) References Cited

U.S. PATENT DOCUMENTS 4,542,751 A 9/1985 Webster et al.
4,635,488 A 1/1987 Kremer
(Continued)

FOREIGN PATENT DOCUMENTS

WO 2018223058 A1 12/2018

OTHER PUBLICATIONS

Kuo, Jonathan TW, et al. "Novel flexible Parylene neural probe with 3D sheath structure for enhancing tissue integration." Lab on a Chip 13.4 (2013): 554-561. DOI: 10.1039/C2LC40935F (Year: 2013).*
(Continued)

*Primary Examiner* — Jonathan T Kuo
(74) *Attorney, Agent, or Firm* — MacMillan, Sobanski & Todd, LLC

(57) ABSTRACT

A wearable biofluid volume and composition system includes a microfluidic flexible fluid capture substrate having a microfluidic channel configured as a sweat collection channel and is configured to be worn on a human body and to collect and analyze biofluid. The microfluidic flexible fluid capture substrate further has a plurality of conductive traces and electrodes. An electronic module is attached to the microfluidic flexible fluid capture substrate and is configured to measure and analyze data from the biofluid collected by the microfluidic flexible fluid capture substrate and to transmit the analyzed data to a smart device.

31 Claims, 25 Drawing Sheets

(51) Int. Cl.
*A61B 10/00* (2006.01)
*A61B 5/11* (2006.01)
*A61B 5/01* (2006.01)
*A61B 5/265* (2021.01)

(52) U.S. Cl.
CPC .............. *A61B 5/01* (2013.01); *A61B 5/1118* (2013.01); *A61B 5/14525* (2013.01); *A61B 5/14546* (2013.01); *A61B 5/265* (2021.01); *A61B 5/4266* (2013.01); *A61B 5/486* (2013.01); *A61B 5/681* (2013.01); *A61B 5/742* (2013.01); *A61B 5/7405* (2013.01); *A61B 5/746* (2013.01); *A61B 5/7455* (2013.01); *A61B 5/7475* (2013.01); *A61B 10/0064* (2013.01); *A61B 2562/0271* (2013.01); *A61B 2562/046* (2013.01); *A61B 2562/166* (2013.01)

(58) Field of Classification Search
CPC . A61B 5/14525; A61B 5/14546; A61B 5/265; A61B 5/4266; A61B 5/486; A61B 5/681; A61B 5/7405; A61B 5/742; A61B 5/7455; A61B 5/746; A61B 5/7475; A61B 10/0064; A61B 2562/0271; A61B 2562/046; A61B 2562/166
See application file for complete search history.

(56) References Cited

U.S. PATENT DOCUMENTS

| | | | |
|---|---|---|---|
| 10,405,794 B2 * | 9/2019 | Begtrup | A61B 5/14546 |
| 10,736,565 B2 * | 8/2020 | Begtrup | A61B 5/201 |
| 10,932,761 B2 * | 3/2021 | Heikenfeld | A61B 5/0531 |
| 2007/0156106 A1 | 7/2007 | Klofta et al. | |
| 2010/0063372 A1 | 3/2010 | Potts et al. | |
| 2010/0132485 A1 | 6/2010 | Erez et al. | |
| 2011/0275918 A1 | 11/2011 | Yamashita et al. | |
| 2014/0276220 A1 | 9/2014 | Briscoe et al. | |
| 2014/0323819 A1 | 10/2014 | Hyde et al. | |
| 2017/0100102 A1 * | 4/2017 | Heikenfeld | A61B 5/14521 |
| 2017/0105646 A1 * | 4/2017 | Bryenton | A61B 5/6824 |
| 2017/0119289 A1 | 5/2017 | Yoshioka et al. | |
| 2017/0296114 A1 | 10/2017 | Ghaffari et al. | |
| 2018/0020966 A1 * | 1/2018 | Begtrup | A61B 5/01 600/301 |
| 2018/0064377 A1 | 3/2018 | Rogers et al. | |
| 2019/0008448 A1 * | 1/2019 | Begtrup | G01N 33/48792 |
| 2019/0246959 A1 | 8/2019 | Ionescu et al. | |
| 2020/0093416 A1 | 3/2020 | Rogers et al. | |

OTHER PUBLICATIONS

International Search Report, Application No. PCT/US2018/062178, dated Feb. 1, 2019.
Koh et al., "A soft, wearable microfluidic device for the capture, storage, and colorimetric sensing of sweat", Science Translational Medicine, 2016, vol. 8, pp. 1-13.
The Extended European Search Report, Application No. 18881519. 5, dated Jul. 19, 2021.

\* cited by examiner

WEARABLE BIOFLUID VOLUME AND COMPOSITION MEASUREMENT SYSTEM

BACKGROUND OF THE INVENTION

This invention relates in general to wearable fluidic systems for collecting, measuring, and/or monitoring biofluid rate, biofluid loss, biofluid volume, biofluid composition, and/or biochemical information about one or more persons. In particular, this invention relates to an improved, wearable fluid collection device for continuous measuring and/or monitoring biofluid volume, rate, and biomarker composition. Such biofluids include, but are not limited to, sweat, wound exudate, blood, interstitial fluid, and urine. Biomarkers include, but are not limited, to sodium, chloride, bacterial load, viral load, pH, glucose, lactate, cortisol, hormones, cytokines, and other proteins.

Access to real-time monitoring of electrolytes, micronutrients, chemical toxins, heavy metals, and metabolites for consumers, industrial workers, athletes, military personnel, firefighters, heart failure patients, kidney failure patients, diabetic patients, cystic fibrosis patients, mental health patients, preterm newborns, and others is critical to mitigate risks of dehydration, other life threatening situations, and diseases, including sepsis, acidosis, anemia, hyperbilirubinemia, and active symptoms of dehydration.

For industrial workers, athletes, military, and emergency personnel, monitoring the rate at which fluids, electrolytes, and other essential body components are lost and consumed during exertion is essential for reducing the risk of injury or death due to dehydration, hyponatremia, or hypernatremia. In many cases the available tools for measuring these fluid body component losses are bulky and non-portable, for example, scales for measuring body weight, and high-performance liquid chromatography (HPLC) for measuring ionic composition. These limitations preclude the measurement of fluid losses at the most relevant times, i.e., when the person being monitored is most active. Real-time monitoring can alert individuals of immediate risk and allow users to conduct preventative measures or remove themselves from the environment.

Point-of-care wearable sensors with real-time data collection and monitoring have the potential to actively measure bioanalyte levels non-invasively, and could shift routine care and metabolite management from a laboratory setting to remote field environments, emergency or intensive care environments, or home settings. Several forms of wearable, electronic, interstitial fluid and sweat analysis systems exploit electrochemical approaches for monitoring biomarker concentrations, but do not allow for real-time monitoring or analysis.

Thus, it would be desirable to provide an improved wearable sweat monitoring system having an improved data transmission system: that allows for real-time analysis and collection of data that overcomes the limitations of current sweat collection systems and conventional wearable sensors, that is high quality, delivers real-time data, and is a readily accessible component of a health monitoring system or work environment monitoring system, that provides diagnostics needed to monitor workers, athletes, patients, etc. in a real time manner outside of the laboratory or clinic, and that can actively report collected data to clinicians, data collection systems, and/or a centralized repository.

SUMMARY OF THE INVENTION

This invention relates to an improved, wearable sweat collection device for continuous measuring and/or monitoring biofluid volume, rate, and biomarker composition and to systems using such devices.

Advantageously, the body-worn sweat and/or biofluid monitoring system described herein can measure biomarkers, volume, location, and temperature of biofluid instantaneously, or over a period of time. The wearable sweat collection system is comprised of a wearable, wireless, electronic measurement module and a complimentary, wearable, flexible, disposable, microfluidic substrate or moisture absorbent material with embedded electrode or electrochemical sensor array.

In one embodiment, a wearable biofluid volume and composition system includes a microfluidic flexible fluid capture substrate having a microfluidic channel configured as a sweat collection channel and is configured to be worn on a human body and to collect and analyze biofluid. The microfluidic flexible fluid capture substrate further has a plurality of conductive traces and electrodes. An electronic module is attached to the microfluidic flexible fluid capture substrate and is configured to measure and analyze data from the biofluid collected by the microfluidic flexible fluid capture substrate and to transmit the analyzed data to a smart device.

In a second embodiment, a wearable biofluid volume and composition system includes a microfluidic flexible fluid capture substrate configured to be worn on a human body. The microfluidic flexible fluid capture substrate includes a flexible substrate body having a first, outwardly facing surface, a second, skin-facing surface, and a sweat collection channel formed therein. The sweat collection channel has a first end defining a sweat inlet port, and a second end defining a sweat outlet port, and a striated adhesive on the skin-facing surface thereof that bonds to skin of a wearer. The striated adhesive defines fluidic channels that prevent sweat from building up underneath the microfluidic flexible fluid capture substrate and further defines an opening having a diameter larger than a diameter of the sweat inlet port, the opening configured to allow sweat to accumulate on the skin and to be forced into the sweat inlet port, and a removable adhesive liner covering the striated adhesive. A first flexible substrate layer has electrical traces, electrodes, and an electrical connector pad printed thereon, and is attached to a surface of the flexible substrate body. A second flexible substrate is attached to a surface of the flexible substrate body opposite the first flexible substrate layer. An upper layer defines a skirt formed from a flexible, soft material that is softer and larger than the flexible substrate body, such that peripheral edges of the skirt extend outwardly beyond a peripheral edge of the flexible substrate body and contacts the skin of the wearer, wherein the portion of the skirt that contacts the skin of the wearer includes an adhesive to adhere to skin, wherein the skirt provides a mechanical transition between a mechanical modulus of the skin to which it is adhered and a modulus of the flexible fluid capture substrate, and wherein the portion of the skirt that contacts the skin includes a plurality of vent holes configured to allow sweat that is not captured in the sweat collection channel to exit from between the flexible fluid capture substrate and the skin to which it is adhered. An electronic module is configured to measure and analyze data from the sweat collected by the microfluidic flexible fluid capture substrate and to transmit the analyzed data to a smart device. The electronic module includes a base, a cover, and a PCB assembly mounted therein, wherein the PCB assembly includes a PCB, a microcontroller, a plurality of functional electronic components mounted to the PCB, and a plurality of electrical connection pins configured to contact the electrical connector pad of the microfluidic flexible fluid capture substrate, a button operative to allow the wearer to deactivate an alarm, and a latch system configured receive and retain the electronic module to the microfluidic flexible fluid capture substrate.

Various aspects of this invention will become apparent to those skilled in the art from the following detailed description of the preferred embodiment, when read in view of the accompanying drawings.

DETAILED DESCRIPTION OF THE PREFERRED EMBODIMENT

The following definitions are provided to clarify their specific use in the context of the invention.

The terms fluidic substrate and microfluidic substrate refer to the substrate component of the device having at least one function or purpose other than providing mechanical support for a component or components disposed on or within the substrate exhibiting microfluidic functionality, such as providing transport of a bodily fluid through or within the substrate, for example via spontaneous capillary action or via an active actuation.

The term moisture absorbing substrate refers to a substrate designed to wick moisture away from one surface.

The term fluidic channel refers to a groove or passage for fluid to flow.

The term fluidic reservoir refers to a recess or cavity into which fluid from the fluidic channel may flow.

The term electrochemical is a descriptive term describing the interaction between chemical change and electrical energy. It includes describing processes or methods whereby current or voltage is generated by a chemical reaction.

The term electrode array refers to several electrode pairs arranged in a geometric formation.

The term smart device refers to a wirelessly connected device that can have custom applications from third party providers, including a smartphone, such as an iPhone™, or a phone running the Android™ operating system, a tablet, such as an iPad, or a smart watch, such as an Apple watch.

The term biofluid refers to a biological fluid. Biofluids may be excreted, such as urine or sweat, secreted, such breast milk, wound exudate or bile, obtained with a needle, such as blood or cerebrospinal fluid), developed as a result of a pathological process, such as blister fluid and cyst fluid, or obtained through other methods.

Figure 1A:
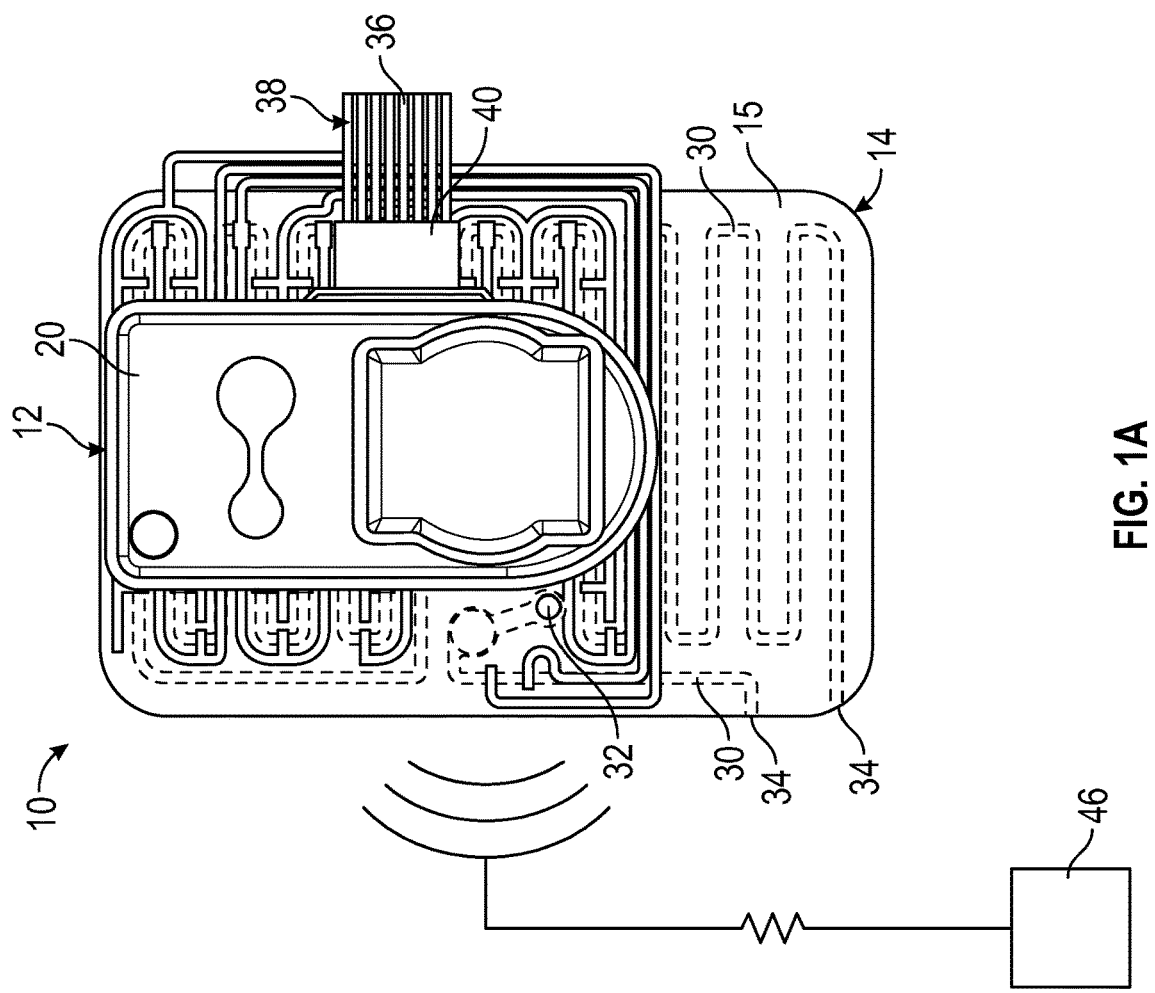
FIG. 1A is an enlarged plan view of the continuous wearable biofluid volume and composition system illustrated in FIG. 1.
Figure 1:
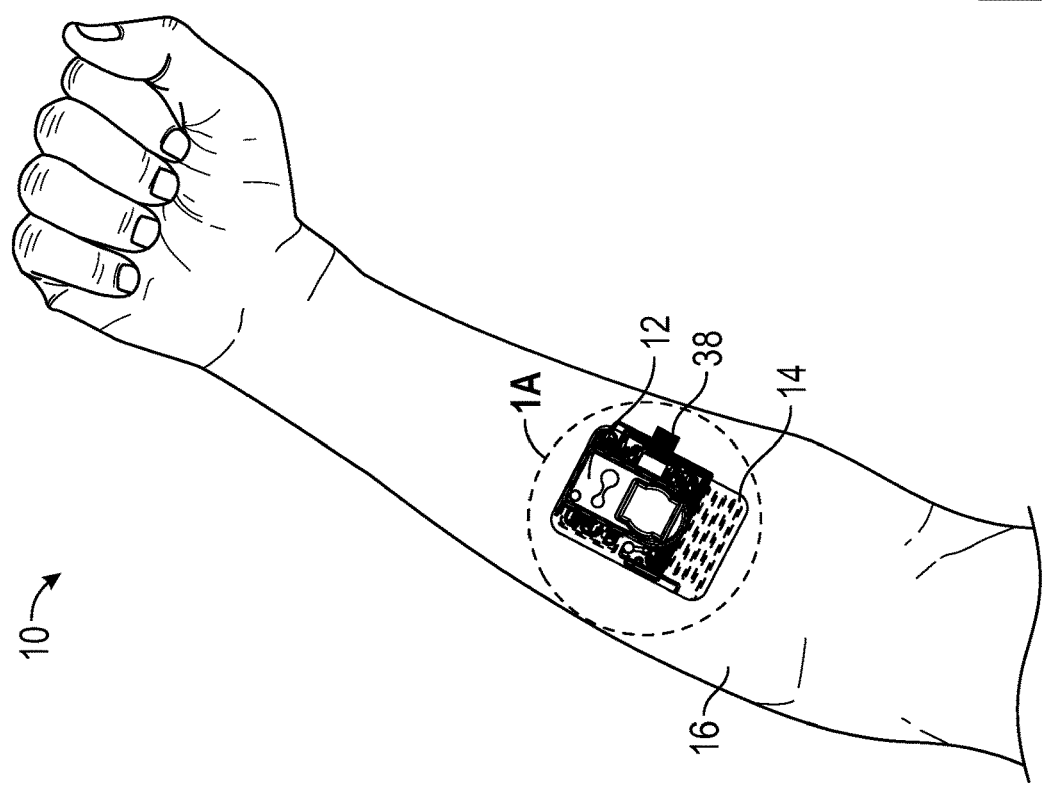
FIG. 1 is a plan view of a first embodiment of a continuous wearable biofluid volume and composition system in accordance with this invention and shown on a user's forearm.

Referring now to FIGS. 1 and 1A, a first embodiment of a continuous wearable biofluid volume and composition system is shown generally at 10. The continuous wearable biofluid volume and composition system 10 includes a first embodiment of an electronic module 12 mounted to a first embodiment of a microfluidic flexible fluid capture substrate 14.

The continuous wearable biofluid volume and composition system 10 according to this invention, and the alternative embodiments thereof disclosed herein, can store measurement data, compute a recommendation, and/or transmit data and/or an assessment wirelessly to a centralized repository or to a local electronic device such as a smartphone, tablet, watch, or personal computer.

As shown in FIG. 1 the continuous wearable biofluid volume and composition system 10 may be worn directly on the user's body, such as the user's forearm 16 shown in FIG. 1.

Figure 2:
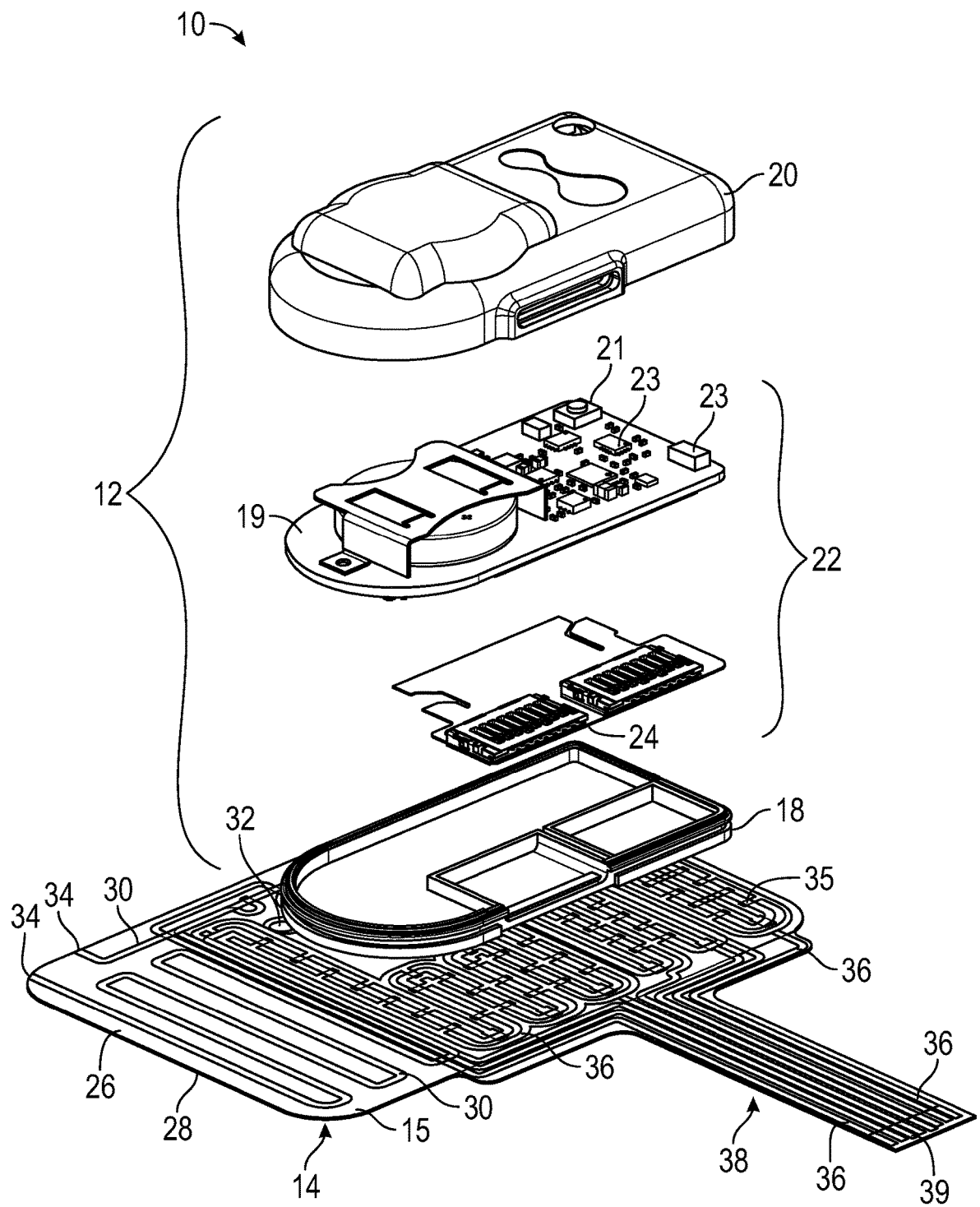
FIG. 2 is an exploded perspective view of the continuous wearable biofluid volume and composition system illustrated in FIGS. 1 and 1A.

As shown in FIGS. 1A and 2, the electronic module 12 includes a base 18, a cover 20, and printed circuit board (PCB) assembly 22 mounted within the electronic module 12. The base 18 and the cover 20 may be formed from any desired rigid plastic material, such as acrylonitrile butadiene styrene (ABS).

The illustrated cover 20 is formed from transparent material, although transparent material is not required. Alternatively, the base 18 and/or the cover 20 may be formed for any other rigid plastic material such as electrostatic dissipative grade acetal copolymers such as Grilon TSC-10/4EC black 9832 or Hostaform® EC140CF-10, and may be formed from opaque, semi-transparent, or transparent material. Additionally, the base 18 and cover 20 may be relatively thin, such as having a thickness within the range of about 1 mm to about 2 mm.

It will be understood that the base 18 and the cover 20 may be designed to be disposable or reusable. Additionally, the cover 20 may be formed from a soft, pliable, or flexible material, such as silicone.

The PCB assembly 22 includes a PCB 19, a microcontroller and other required functional electronic components 23, also described below, mounted to the PCB 19 and necessary to operate the electronic module 12. As shown in FIG. 2 the PCB assembly 22 includes an on/off button 21 and an electrical socket 24. The illustrated electrical socket 24 is a microSD® socket. Alternatively, the electrical socket 24 may be any desired conventional electrical socket.

The flexible fluid capture substrate 14 may be configured to be worn on a human body and includes a flexible substrate body 15 having a first, outwardly facing surface 26, a second, skin-facing surface 28, and one or more sweat collection or microfluidic channels 30 formed in the flexible substrate body 15. Each microfluidic channel 30 has a first end defining a sweat inlet port 32, and a second end defining a sweat outlet port 34. The skin-facing surface 28 includes an adhesive that bonds to skin of the wearer, and the skin-facing surface 28 is covered by a removable adhesive liner (such as shown at 134 in FIG. 9) formed from any desired flexible material, including but not limited to an air/oxygen impermeable material. Although not shown in the illustrated flexible fluid capture substrate 14, one or more fluidic reservoirs may be formed in the flexible fluid capture substrate 14. Such a fluidic reservoir may be configured as a recess or cavity into which fluid from the fluidic channel may flow.

As shown in FIG. 1, the flexible fluid capture substrate 14 is configured to conform to the contours of the human body.

An area around the inlet port 32, on the skin-facing surface 28, may be free of adhesive to provide an area wherein sweat pools or accumulates on the skin and is forced into the microfluidic channel 30.

The flexible fluid capture substrate 14 may be formed in one or more layers, such as three layers or five layers from a desired flexible material, including but not limited to silicone, clear polyester, polyethylene terephthalate (PET), and thermoplastic polyurethane (TPU). Examples of methods in which the flexible fluid capture substrate 14 may be formed have been described and illustrated in PCT Application No. PCT/US18/43430, the disclosure of which is incorporated herein by reference.

Electrodes 35, formed in an electrode array, and/or one or more electrical trace 36 may be printed on either or both sides of the flexible fluid capture substrate 14, i.e., the outwardly facing surface 26 and the skin-facing surface 28, if the printed array of electrodes 35 and the electrical traces 36 can make contact with the biofluid. An electrical connection is maintained through the use of a via hole (not shown) cut into the flexible fluid capture substrate 14 and a via fill (not shown) that closes an electrical connection between a top and bottom layer of the flexible fluid capture substrate 14. In this manner, the traces 36 may be routed to avoid contact with fluid in the microfluidic channel 30, thus eliminating the need for a dielectric coating layer on the traces 36. Alternatively, the traces 36 may be routed such that the traces 36 are compatible with certain types of connectors (not shown), such as Mill-Max 8xx series spring-loaded connectors (such as shown at 180 in FIG. 11 and at 184 in FIG. 12), or Bournes 70AA series contact wipe connectors (not shown). In one embodiment, the electrodes 35 of the electrode array (not shown) and the traces 36 are formed from a stretchable silver paste printed on the flexible substrate body 15. Alternatively, the electrodes 35 and the traces 36 may be formed from any desired conductive material, including but not limited to gold.

Figure 6:
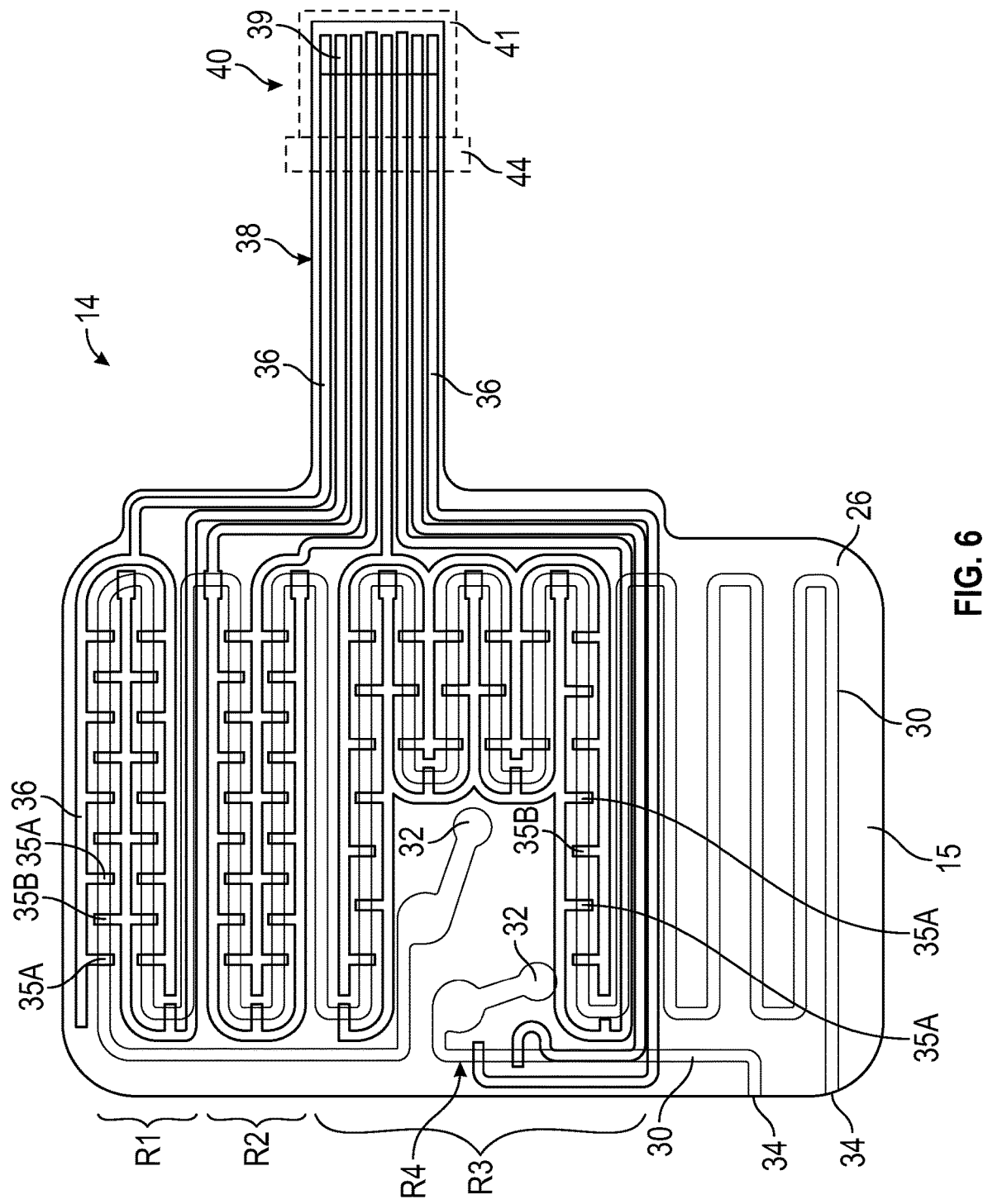
FIG. 6 is an enlarged plan view of a first embodiment of the flexible fluid capture substrate illustrated in FIGS. 1, 1A, and 2.

A ribbon cable 38 extends outwardly from the flexible substrate body 15 and is formed from the same material as the substrate body 15. Portions of the traces 36 are formed on the ribbon cable 38. Distal ends of the traces 36 in the ribbon cable 38 are exposed and define conductive connector pads 39. As shown in FIG. 6, the ribbon cable 38 may include a microSD® connector 40. Alternatively, the ribbon cable 38 may include other connectors, including but not limited to a zero insertion force (ZIF) style connector, a perpendicular style connection formed from conductive micro hook and loop, and electrically conductive adhesive transfer tape, such as z-axis conductive tape. When the ribbon cable 38 includes the microSD® connector 40, a distal end of the ribbon cable 38 may include a stiffener 41 and may also include a gasket 44 configured to mate with the microSD® socket 24.

If desired, any exposed electrode or electrode pads, such as the electrodes 35, may have an additional Ag/AgCl coating to reduce or provide low junction potential at the ion/electrical barrier. Alternatively, any exposed electrode may be coated with any material that causes the electrode to be non-polarized and have a low junction potential.

A dielectric coating may be applied to the electrodes 35 and the traces 36 to prevent inadvertent electrical pathways to the microfluidic channel 30 in the flexible substrate body 15, thus allowing signal pathways when the traces 36 are in contact with fluid in the microfluidic channel 30.

It will be understood that the one or more microfluidic channels 30 formed in the flexible substrate body 15 may include, but do not require, the incorporation of a specific channel geometry to dampen the flow of the sweat therethrough. Examples of such geometry include but are not limited to baffles, valves, and the like (not shown), designed to prevent backflow and/or excessive sweat movement not related to the wearer's sweat rate or excretion.

If desired, a sub-assembly (not shown) comprising an array of sensors, electrodes, copper or conductive metallic electrodes, printed conductive electrodes, and/or conductive electrodes may be formed in the one or more layers of the flexible substrate body 15, may be exposed or formed in the microfluidic channel 30, and may be positioned to contact the fluid traveling through the microfluidic channel 30.

As also shown in FIG. 1A, the electronic module 12 is configured to transmit data collected wirelessly to a smart device 46, schematically illustrated in FIG. 1. Examples of the type of collected and/or computed data that may be displayed on the smart device 46, such as an Apple watch, are shown in FIGS. 15A through 15F.

Figure 3:
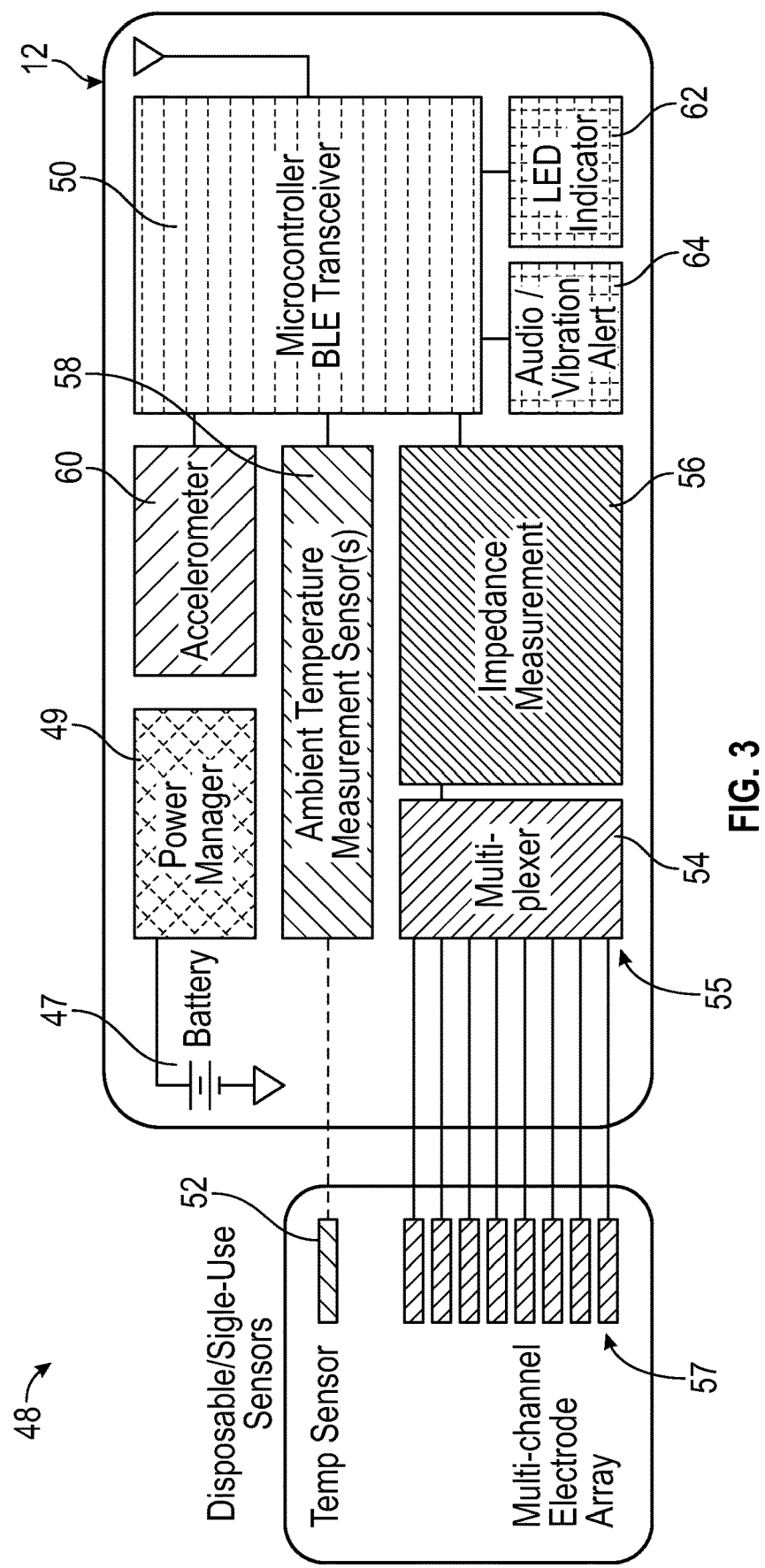
FIG. 3 is a simplified circuit block diagram of the electronic module of the continuous wearable biofluid volume and composition system illustrated in FIGS. 1, 1A, and 2.

Referring now to FIG. 3, a simplified circuit block diagram is shown at 48, and illustrates the functional blocks of the re-usable electronic module 12. The electronic module 12 is powered by a battery 47 connected to a power manager 49, and is able to continuously measure, log, and wirelessly transmit data to a networked central hub (not shown) and/or the smart device 46 via a transceiver, such as a 2.4 GHz Bluetooth Low Energy (BLE) 5.1 transceiver 50. Alternatively, other means of data transmission may be used, such as ANT, 802.11, Zigbee, and other transceivers including transceivers based on IEEE 802.15.4 standards. Sensors 52 provided in the electronic module 12 include, but are not limited to, temperature, motion, electro-impedance spectroscopy of a fluid, amperometric measurement of current during oxidation or reduction, and/or potentiometric measurements during a chemical reaction. The sensors 52 may be disposable or single-use sensors. A multiplexer 54 switches the electro-impedance spectroscopy, via an impedance measurement circuit 56, between several electrode pairs 57. This allows multiple regions on the complimentary flexible fluid capture substrate 14 to be measured.

While an on-board temperature sensor 58 placed on the skin side of the electronic module 12 is included, an additional, optional, temperature sensor (not shown) may be incorporated into the flexible fluid capture substrate 14.

Additional sensors not related to fluid biomarker measurements may be included, such as an accelerometer 60 which adds insight to fluid flow in response to the wearer's motion. The measurement and collection of wearer motion serves multiple purposes. A first purpose is to assess and reject motion artifacts during a measurement. A second purpose is to capture the wearer's motion and compare that value to a correlated set of values empirically derived and modeled to evaluate the wearer's physical intensity, also known as workload.

Alarms and indicators may be provided and include LEDs 62, and may also include non-visual indicators such as audio or vibration alerts 64 when an on-board algorithm detects that certain, pre-determined, biomarker concentrations, and/or volume thresholds have been met.

Additionally, the electronic module 12 is configured to measure biomarker characteristics and combine the measured biomarker characteristics with time, for example from a timer, to provide an output comprising temporal data, for example the onset and end of sweating. The electronic module 12 is also configured to measure biomarker characteristics and combine the measured biomarker characteristics with temperature measurements to calibrate parameters such as volume fill. The electronic module 12 is further configured to measure biomarker characteristics and combine the measured biomarker characteristics with motion measurements to reject volume measurement fluctuation and to provide biomarker and fluid volume recommendations. Additionally, the electronic module 12 is configured to measure motion values that have been correlated to specific work task activities or athletic activity workloads, such as physical intensity, which may then be used as inputs in a rehydration recommendation algorithm and a rehydration alert warning algorithm.

Figure 4A:
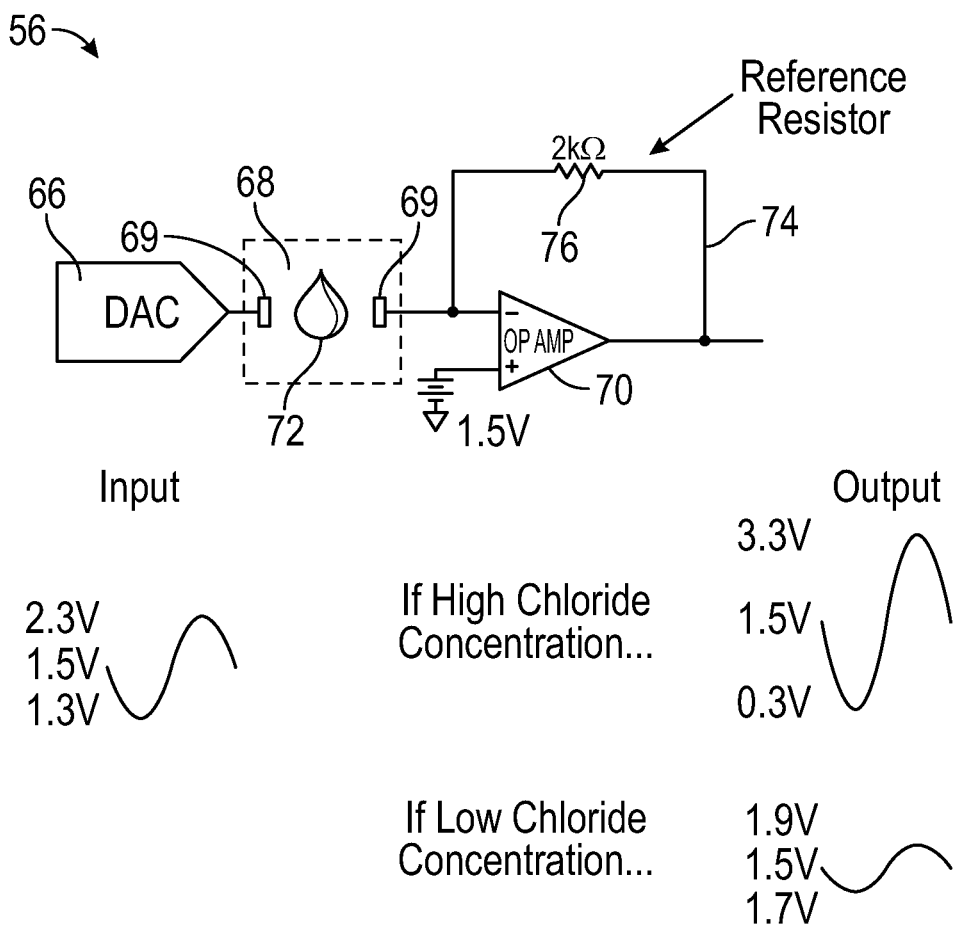
FIGS. 4A and 4B are circuit diagrams of an embodiment of a circuit configured to measure sweat conductivity.
Figure 5A:
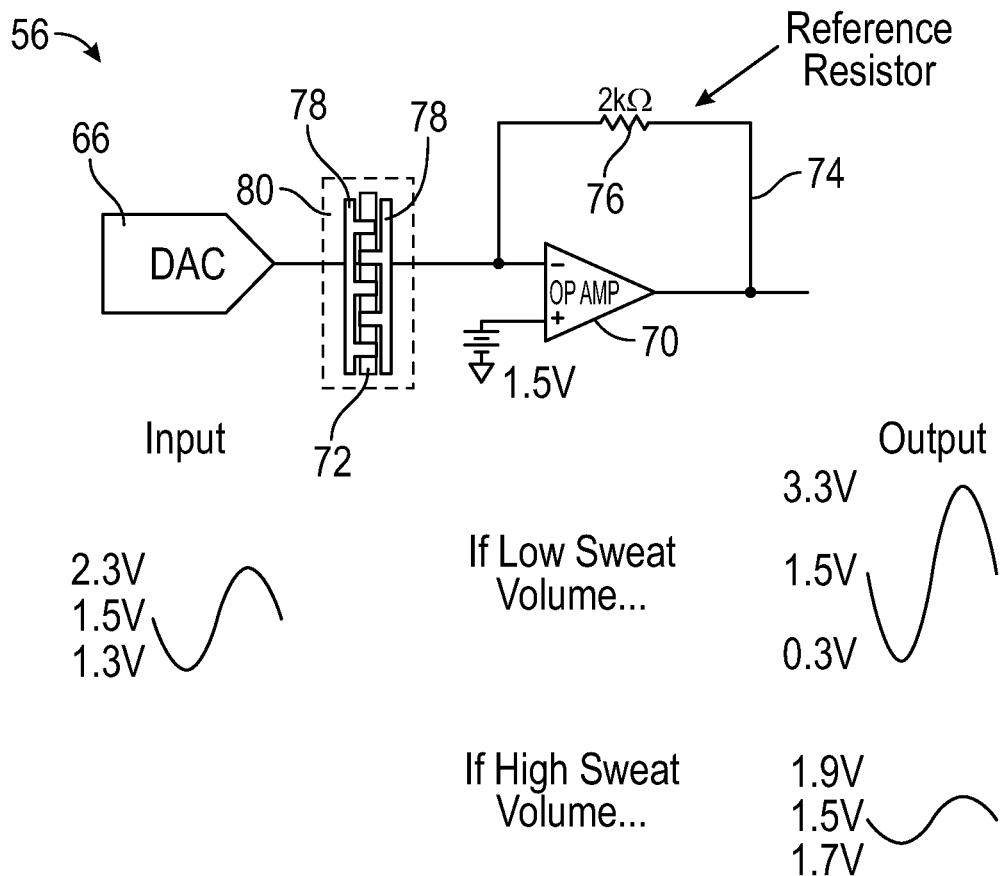
FIGS. 5A and 5B are circuit diagrams of an embodiment of a circuit configured to measure sweat fill volume.

The electro-spectroscopy obtained via the impedance measurement circuit 56 is shown in FIGS. 4A and 5A. As shown, two types of data may be collected using the same impedance measurement circuit 56. As shown in FIG. 4A, digital to analog converter (DAC) 66 generates an excitation sinusoid voltage onto an electrode pad 68 having two electrode plates 69. Any conventional DAC may be used, including, but not limited to, an AD5641AKSZ integrated circuit (IC) manufactured by Analog Devices, Inc. The complimentary electrode pad 68 is connected to an operational amplifier's (op amp) 70 negative terminal, where the op amp 70 is configured as a transimpedance amplifier. Any conventional op amp may be used, including, but not limited to, an LTC6255 op amp manufactured by Analog Devices, Inc. A mid-scale DC bias voltage set by the op amp 70 determines the voltage drop across the electrode dielectric. When a biofluid such as sweat 72 is between the electrode plates 69, the voltage drop across the biofluid, such as the sweat 72, generates a current. The current generated enters a transimpedance amplifier circuit 74 and the current flows into the reference resistor 76. In its simplest form, the resistance of the biofluid 72 may be represented by the equation:

$$R\_Biofluid = R\_Ref\ Input/Output$$

The transimpedance amplifier circuit 74 as shown in FIG. 4A measures sweat conductivity. However, FIG. 5A illustrates that by using a different fluidic channel and a different shape electrode 78, unlike the transimpedance amplifier circuit 74 as shown in FIG. 4A, the sweat fill volume may be determined because the resistance decreases as fill volume increases. An output is then digitized using an analog to digital converter (ADC) (not shown). In the simplest form, a sinusoid at a fixed frequency of 10 kHz is generated and sent through the electrode pad 80. A corresponding current is then passed across the biofluid 72 and is measured on the electrode pad 80 by the transimpedance amplifier circuit 74, such as may be constructed from an operational amplifier, LTC6255, which converts the current to a voltage that is measured by the ADC which digitizes the signal, and subsequently, a microcontroller (not shown) computes the resistance, or real value, of the biofluid 72. The DAC 66 however, may be programmed to sweep from a high to a low frequency in addition to adjusting voltage magnitude, and the transimpedance amplifier circuit 74 can measure both the magnitude and the phase. Impedance may be measured by capturing phase information of the output waveform in addition to the magnitude of the output waveform, allowing the complex impedance to be measured and gaining an additional characteristic signature of the biofluid 72 sample.

Figure 4B:
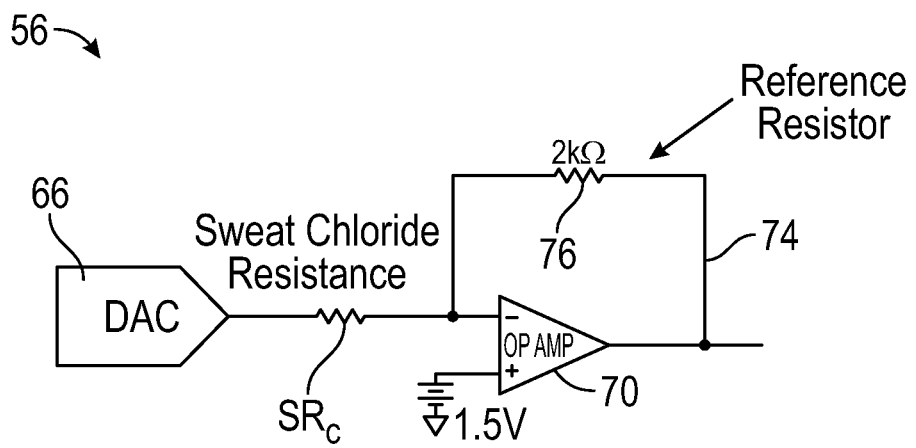
Figure 5B:
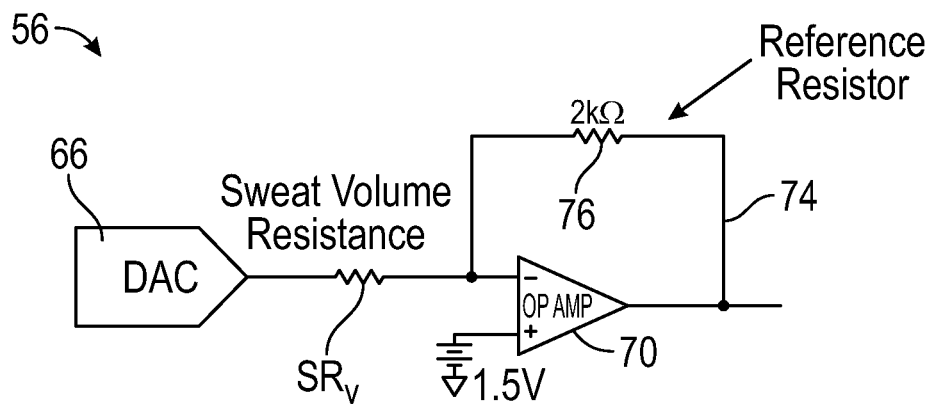

In FIG. 4B, the op amp 70 signal indicates that the sweat conductivity resistor value $SR_C$ is a fraction or a multiple of the reference resistor 76. Similarly, in FIG. 5B, the op amp 70 signal also indicates that the sweat volume resistor value $SR_V$ is a fraction or a multiple of the reference resistor 76.

Referring again to FIG. 3, the multiplexer 54 may be any conventional multiplexer configured to switch measurement circuit inputs 55 between the several electrode regions 57, including but not limited to TMUX1208 and TMUX1209 multiplexers manufactured by Texas Instruments. Additionally, the electronic module 12 may use one or more of the inputs 55 to measure conductivity, such as NaCl, or to calibrate volume readings. Additional inputs 55 in the multiplexer may be used to switch between several electrode pairs 57 comprising multiple regions on the flexible fluid capture substrate 14.

In some embodiments of the electronic module 12, a 3 electrode or 4 electrode measurement may be made using a potentiostat configuration using conventional, discrete operational amplifiers, instrumentation amplifiers, digital to analog converters, and/or using an integrated IC solution including but not limited to the MAX30208 electrochemical frontend sensor and the AD5940 analog frontend, both manufactured by Analog Devices.

The reusable electronic module 12 can continuously measure, store, and wirelessly transmit data to the networked central hub (not shown) and/or the smart device 46. Such data may include information regarding sensing capabilities which include, but are not limited to, temperature, motion, electro-impedance spectroscopy of a fluid, amperometric measurement of current during oxidation or reduction, and/or potentiometric measurements during a chemical reaction.

As shown in FIGS. 3, 4A, 4B, 5A, and 5B, the reusable electronic module 12 measures electro-impedance by exciting a voltage across a fluid through two electrodes and measuring the corresponding current using a transimpedance amplifier circuit. In these embodiments, the voltage of the excitation sinusoid signal and the transimpedance amplifier input is centered around the mid-scale voltage, 1.5V. The excitation voltage is generated by the DAC 66 with a maximum peak to peak sinusoid voltage of 3.0V peak-to-peak. The DAC 66 is configured such that any waveform shape may be programmed, and multiple frequencies may be generated. In one embodiment, a sinusoid at a fixed frequency of 10 kHz may be generated and sent through an electrode pad. A corresponding current may then be passed across the fluid and measured on a complimentary electrode pad by a transimpedance amplifier which converts the current to a voltage that is ultimately converted by an ADC which digitizes the signal. The microcontroller 23 on the PCB assembly 22 computes the resistance, or real value, of a fluid (see FIGS. 4B and 5B). However, the DAC can be programmed to sweep from a high to low frequency in addition to adjusting voltage magnitude and the transimpedance amplifier can measure both the magnitude and phase, allowing the complex impedance to be measured gaining an additional characteristic signature of the fluid sample.

The electronic module 12 includes the multiplexer 54 to accept signals from several electrode pairs, for example the electrode plates 69 and the electrode plates 78 while using the same signal conditioning and measurement circuit, and keeping offsets and any errors consistent across all inputs. In addition, the multiplexer may switch between different types of measurements, for instance between an NaCl molarity measurement and a volume measurement.

Advantageously, the electronic circuit within the electronic module 12 is configured to measure the volume of biofluid in the physiological range from about 1 µL to about 100 µL, and the quantity of sodium in the physiological range from about 1 mg to about 1 g.

Figure 7A:
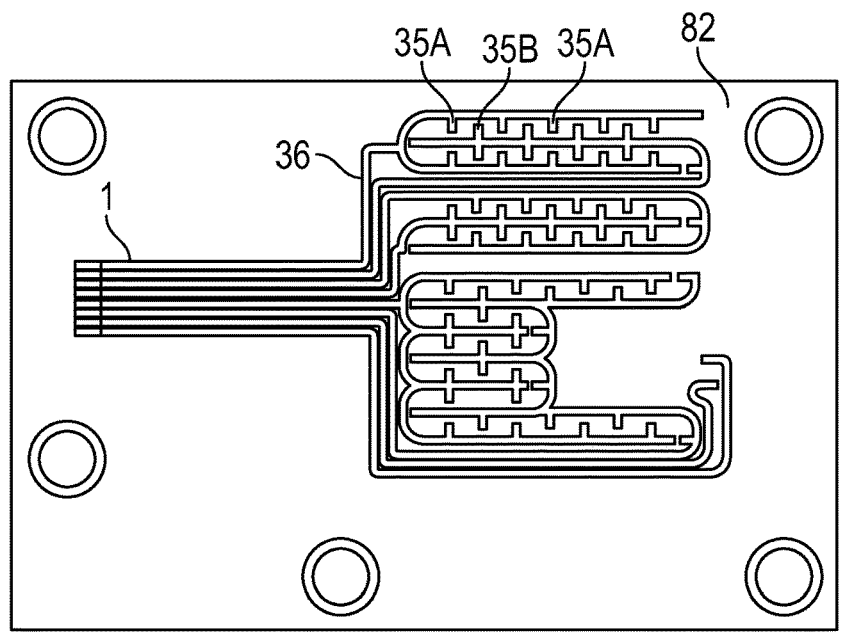
FIG. 7A is a plan view showing the electrode array and traces formed on a clear substrate.

FIG. 7A shows the electrode array 35 and traces 36 formed on a flexible clear substrate 82. Materials that may be used to form the clear substrate 82, include, but are not limited to, polyethylene terephthalate (PET), clear polyester, and thermoplastic polyurethane (TPU), such as Dupont Intexar TE-11C TPU. The illustrated substrate 82 has a thickness of about 3 mil. Alternatively, the substrate 82 may have a thickness within the range of about 2 mil to about 4 mil. The illustrated electrodes 35 and traces 36 are formed from a stretchable silver paste printed on the flexible clear substrate 82. Alternatively, the electrodes 35 and the traces 36 may be formed from any desired conductive material, including but not limited to silver and gold.

The junction overpotential of the electrodes 35 and traces 36 may be reduced by applying an Ag/AgCl coating. For example, as shown in FIG. 7A, exposed electrode pads 35A have an additional Ag/AgCl coating, such as DuPont 5880, to reduce or provide low junction overpotential at the ion/electrical barrier. The traces 36 have a dielectric coating, such as DuPont PE773, applied thereto to prevent inadvertent electrical pathways to the microfluidic channels 30 in the microfluidic substrate, such as the flexible fluid capture substrate 14, allowing the traces 36 to provided unimpeded signal pathways when in contact with fluid in a microfluidic channel 30.

Figure 7B:
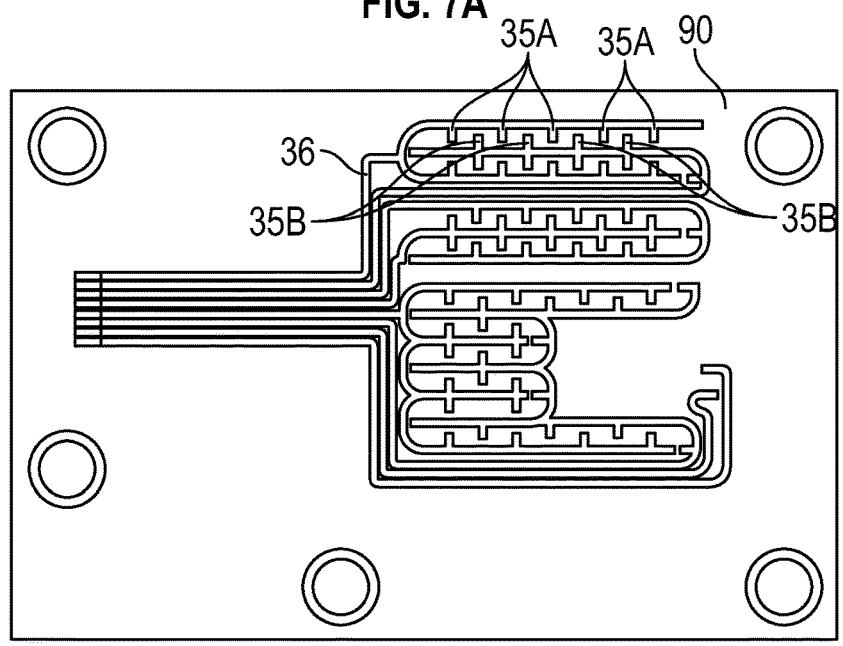
FIG. 7B is a plan view showing the electrode array, traces, and clear substrate illustrated in FIG. 7A bonded to an opaque substrate layer.
Figure 7C:
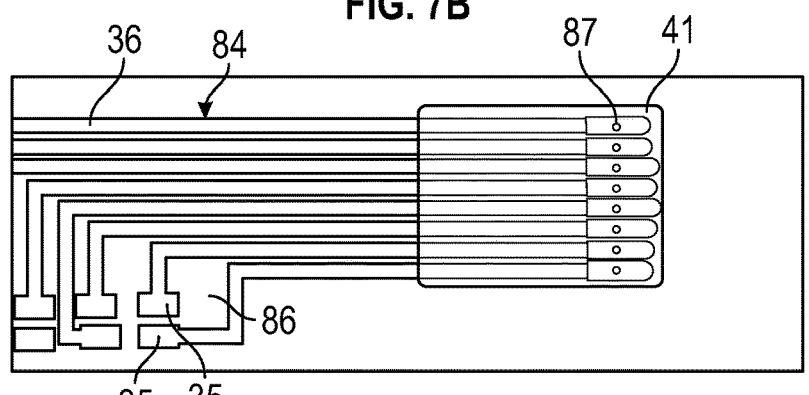
FIG. 7C is a plan view of a portion of an embodiment of the electrode array and traces formed on a clear substrate and showing the ribbon cable.

The material used to form the clear substrate 82 is also used to form the ribbon cable 84 shown in FIG. 7C. A distal end of the ribbon cable 84 has the stiffener 41 and may also include the gasket 44 (as shown in FIG. 6) configured to mate with the microSD® socket 24. The stiffener 41 is attached, such as by gluing, to the non-conductive side of an alternate embodiment of the ribbon cable 84 to facilitate easy insertion into the microSD® socket 24. Additionally, the stiffener 41 may be keyed to prevent improper insertion.

FIG. 7C shows a portion of an embodiment of the electrode array 35 and traces 36 formed on a clear substrate and showing the ribbon cable 84. As also shown in FIG. 7C, the electrical traces 36 may be formed on one surface, such as the outwardly facing surface of the substrate 82 (the downwardly facing surface when viewing FIG. 7C) and be electrically connected to the other surface, such as the skin-facing surface 86, by using a via 87. The via 87 is configured as a hole cut into the substrate 82 and filled with enough conductive material to allow electrical conduction from one surface to another surface. In this manner, the traces 36 may be routed to avoid contact with fluid, thus eliminating the need for a dielectric layer coating. Also, the traces 36 may be routed such that the traces 36 are compatible with other conventional types of connectors (not shown). The vias 87 connect the traces 36 on outwardly facing surface 86 to the conductive connector pads 88 on the skin-facing surface 86.

As shown in FIG. 7B, an array of the electrode pads 35A, traces 36, and clear substrate 82 are bonded to an opaque substrate layer 90. The electrode pad 35A and 35B spacing is designed to ensure easy manufacturing alignment and to increase adjustment of conductivity by placing the electrode pads 35A and 35B in a zipper configuration. By placing the electrode pads 35A and 35B in the path of the biofluid in the microfluidic channels 30, rather than alongside the walls of the microfluidic channels 30, manufacturing alignment tolerances are eased because the size of the electrode pads 35A and 35B can increase axially along the fluid channel. For example, as shown in FIG. 7B, each individual electrode pad 35A and 35B defines a tooth, and an electrode pair includes two sets of meshing teeth, much like a zipper. Thus, the configuration of the electrodes and traces allow for greater misalignment of the traces with the fluidic channel during manufacturing, yet maintaining maximum electrode contact with fluid in the microfluidic channels 30.

In FIG. 7B, positive electrode pads or teeth are shown at 35A, and negative electrode pads or teeth are shown at 35B. As shown, the electrode pads 35A are interwoven with the electrode pads 35B. The electrode pads or teeth 35A and 35B are the only elements of the electrode structure contacting the biofluid in the channel. In contrast, if the electrode pads 35A and 35B instead ran alongside the microfluidic channel 30, the channel width may have to be undesirably increased to ensure electrode pads 35A and 35B contact with biofluid reducing volume captured. Alternatively, the channel height may be increased, however the rigidity of the fluidic substrate would then have to be increased to maintain structural integrity of a taller channel, both options of which may have unfavorable effects on the flexibility and performance of the fluidic substrate.

Another advantage of forming the electrode pads 35A and 35B in the zipper configuration is that the electrode area in contact with the biofluid is reduced. The more contact with the biofluid, the lower the impedance, thus requiring higher resolution signal conditioning. By limiting electrode pads 35A and 35B contact with the biofluid, and by placing the electrode pads 35A and 35B at discrete intervals, the illustrated design reduces complexity and cost. Additionally, the electrode pads 35A and 35B, or teeth, are interwoven and as biofluid flows through the microfluidic channel 30, the signal changes in discrete time intervals or steps. These discrete steps provide an additional identifier of the sweat fill volume.

Although the zipper-shaped electrode design makes it conducive to count steps, there remains a challenge that there will be subjects who have low salinity sweat which has high resistance, and other subjects who have high salinity sweat which has low resistance. The sweat fill volume that the impedance measurement circuit 56 (see FIG. 3) can measure for high salinity sweat is lower than the sweat fill volume for a low salinity subject. To maximize the amount of volume the impedance measurement circuit 56 can measure, the spacing between the electrode pads 35A and 35B may be increased and/or the electrode pad area made smaller in size to increase the resistance of the biofluid measurement and increase volume of biofluid measured in a microfluidic channel 30.

Figure 8:
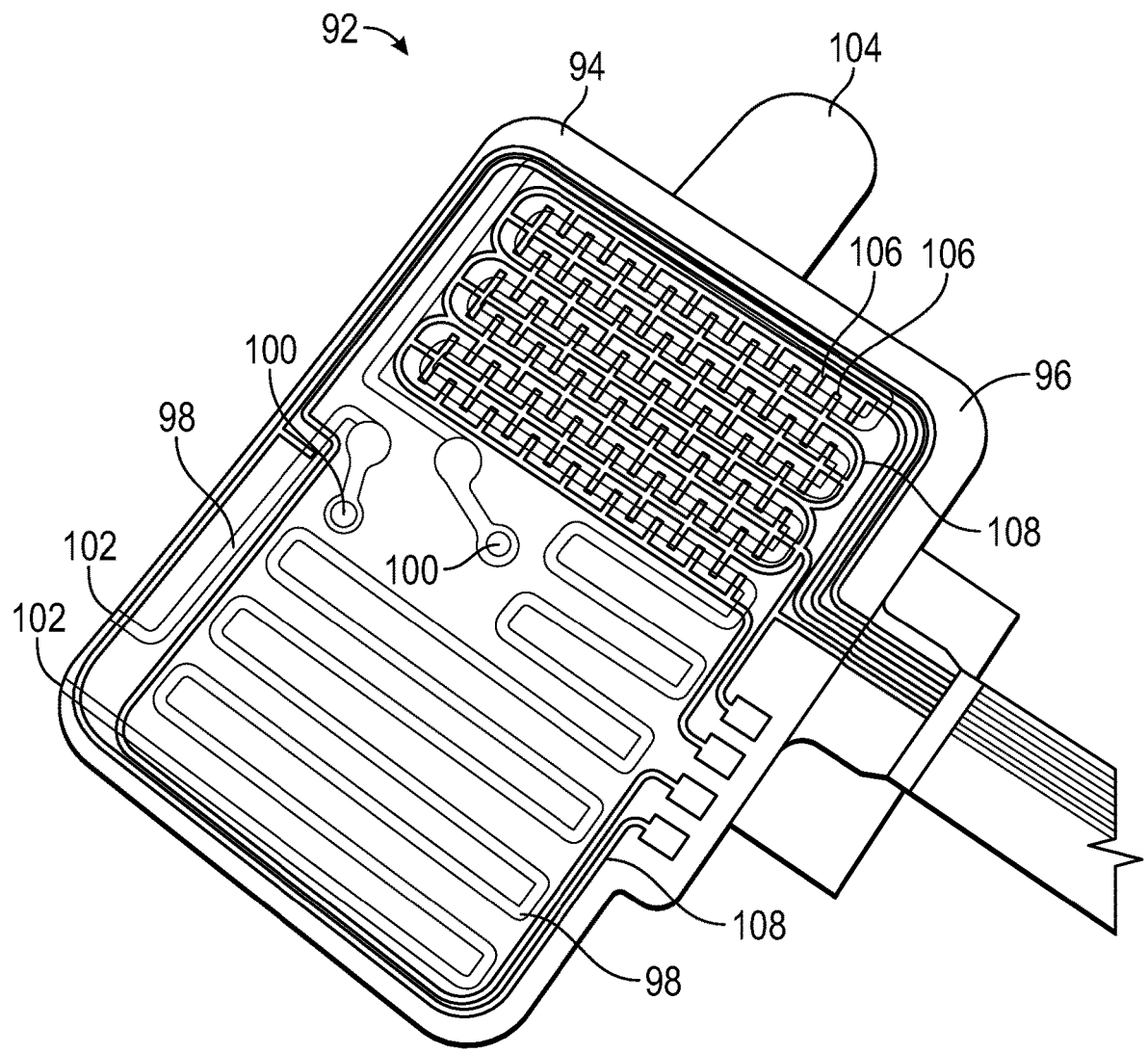
FIG. 8 is a perspective view of a second embodiment of the flexible fluid capture substrate illustrated in FIGS. 1, 1A, 2, and 6.

Referring now to FIG. 8, a second embodiment of the flexible fluid capture substrate is shown at 92. The flexible fluid capture substrate 92 is similar to the flexible fluid capture substrate 14 and may be configured to be worn on a human body. The flexible fluid capture substrate 92 includes a flexible substrate body 94 having a first, outwardly facing surface 96, a second, skin-facing surface (not shown), and one or more sweat collection or microfluidic channels 98 formed in the flexible substrate body 94. Each microfluidic channel 98 has a first end defining a sweat inlet port 100, and a second end defining a sweat outlet port 102. The skin-facing surface (not shown) includes an adhesive that bonds to skin of the wearer, and may be covered by a removable adhesive liner, a portion of which is shown at 104, formed from any desired flexible and air/oxygen impermeable material. Electrodes 106 and one or more electrical traces 108 may be printed on either side of the flexible fluid capture substrate 92, as described in detail above.

In another embodiment, the measurement signal path may be multiplexed such that a single microfluidic channel 30 is measured by several, sequential, measurement regions, wherein the multiplexer 54 switches between the various sequential electrode pad pairs 35A and 35B. As the biofluid flows through the microfluidic channel 30, its resistance is measured by an electrode pad pair 35A and 35B. At a predetermined point along the microfluidic channel 30, the initial electrode pad pair 35A and 35B ends and a new electrode pad pair 35A and 35B begins measuring biofluid, as shown in FIG. 7B. This process may be repeated with consecutive electrode pad pairs 35A and 35B. By limiting the amount of biofluid measured by each electrode pad pair 35A and 35B, the resistance does not fall below the threshold of the ADC.

In FIG. 6, three regions R1, R2, and R3 are shown in a single first fluidic channel 30, and it is within each of these regions R1, R2, and R3 that biofluid measurements are obtained. A fourth region R4 is shown in a second microfluidic channel 30 within which additional biofluid measurements are obtained. In one embodiment, the space between electrode pads 35A and 35B in the first and second regions R1 and R2 is 2 mm. In the third region R3, the space between electrode pads 35A and 35B is 3 mm. It will be understood that the pitch between electrode pads 35A and 35B, and the area of the electrode pads, may be adjusted as required in different embodiments of the continuous wearable biofluid volume and composition system 10. For example, the pitch and area may be adjusted or optimized to measure a large captured volume of biofluid and/or to measure finer volume intervals, such as intervals within about 1 mm to about 4 mm. Significantly, since it is known that when sweat enters each successive region, for example region R2 or R3, discrete volume thresholds have already been reached, then by the time fluid enters the region R2, the volume in region R1 may be about 15 μL in some embodiments.

When multiplexing and/or measuring several regions R1, R2, and R3 along the same microfluidic channel 30, each region R1, R2, and R3 undergoes a change in signal magnitude and/or phase in sequential order over time. For example, the biofluid, i.e., sweat, first fills the microfluidic channel 30 within the first region R1, wherein the biofluid is measured. The biofluid then proceeds along the first microfluidic channel 30 to the area within the second region R2, wherein the biofluid is measured. Subsequently, the biofluid proceeds along the first microfluidic channel 30 to the area within the third region R3, wherein the biofluid is again measured. In the embodiment illustrated in FIG. 6, the magnitude of the measurements within the first region R1 changes first, followed by the magnitude of the measurements within the second and third regions R2 and R3, in sequential order. When plotted over time, the volume of biofluid is measured by a single contiguous electrode pad pair 35A and 35B. Advantageously, each region R1, R2, and R3 is capable of measuring with a high resolution to discern small changes in volume for high sodium-chloride (conductivity) biofluid, which would not be the case if a single region were used to measure the entire volume. In another embodiment, the DAC and ADC resolution may be increased, and the transimpedance amplifier noise reduced, to ensure higher signal to noise and a greater ability to measure high NaCl sweat in a larger volume.

Referring again to FIG. 6, the electrode pads 35A and 35B may be spaced differently within each region R1, R2, and R3. In such an embodiment, the impedance computation would then be adjusted for the different pitch. In the third region R3, a wider pitch allows for measuring a larger total fluid fill volume before the signal falls below the resolution of the ADC at the cost of fewer incremental measurements as biofluid fills the microfluidic channel 30. A narrower pitch allows for more incremental measurements as fluid fills but has the disadvantage of reaching a smaller total volume fill before falling below the ADC's minimum resolution threshold. In one embodiment, the electrode pads 35A and 35B in a given region are designed with 2 mm spacing between the electrode pads 35A and 35B, and with a fluid contact area pad of 1×1 mm to measure a 26 µL volume for within the range of about 10 mM sodium chloride to about 90 mM sodium chloride while maintaining resolution for 0.5 µL increments. Increasing the electrode pad 35A and 35B spacing also referred to as pitch, as shown in the third region R3, would increase the increment interval value and also increase the total volume measured with a single electrode pad pair 35A and 35B. However, the wider pitch is used for the third region R3 after fine granular, volume interval measurements have been made in the prior regions R1 and R2.

In another embodiment, for example in the flexible fluid capture substrate 92 shown in FIG. 8, the electrodes 106 are spaced 1 mm apart. Thus, measurements taken with the flexible fluid capture substrate 92 and with the flexible fluid capture substrate 14 will have smaller electrical magnitude readings than similar substrates with wider spaced electrodes for the same NaCl molarity of a biofluid sample.

When measuring the volume of a fluid such as sweat across individuals, there is a range of conductivity levels and differing sweat rates. Advantageously, this invention provides an improved ability to measure an amassed fluid volume with high precision, at low-cost, while minimizing the number of electrical connections to the electrodes. As sweat increasingly fills the dielectric between electrode pads, the resistance measured in that fluid volume decreases, if measured across electrodes with fixed dielectric spacing. There is a finite limit at which the ADC can measure. Further complicating the measurements is that low NaCl sweat has a high resistance and can fill a larger volume before falling below the minimum resolution of the ADC while high NaCl sweat has low resistance and fills a smaller volume before falling below the minimum resolution of the ADC.

In one embodiment, the spacing and electrode pad area may be designed such that the measurement is more sensitive in the beginning since most people can sweat or fill the early region with sweat or biofluid and later regions (if in sequential order) have wider spaced pitch to be able to measure more fluid at the expense of less sensitivity since much of the data has been computed by earlier regions and in later regions the interest is the fluid front or the maximum volume expelled.

As described above, computed data may be displayed on a smart watch, as shown in FIGS. 1A and 15A through 15F. Additionally, an alert delivered to the smart watch, such as by vibration, sound or other audible acoustic signals, lights, such as flashing lights, and/or text or other visual notification on a smart device display screen, indicates whether a course of action should be taken. For example, when the wearable biofluid volume and composition system 10 is worn by an athlete or a worker, one course of action may be for the wearer to stop and rehydrate with a proposed electrolyte fluid mixture. In another example, a course of action may be for a caretaker to replace a wound care dressing, described below in detail, because the dressing is filled with biofluid and is no longer at optimal condition.

Computed data may also be displayed in real-time on a smartphone (not shown). For example, the smartphone may display whole body sweat loss (mL), sweat sodium loss (mg), skin temperature (Celsius or Fahrenheit), heart rate, and other data. An athlete or worker may desire to track their sweat biomarkers, including but not limited to sweat sodium. Software in a smartphone application may, for example, allow data from across multiple wearers, to be displayed. Such data includes, but is not limited to information about device range, overall sweat loss, including low sweat loss, moderate sweat loss, and heavy sweat loss. Such real time sweat data can be used to track dehydration and heat stress in the context of industrial work, athletics, or clinical care for tracking dehydration in elderly care patients, cystic fibrosis patients, or heart failure patients undergoing physical rehabilitation.

In some embodiments of the wearable biofluid volume and composition system described herein, there is a method of logging fluid and electrolytes consumed via the smartphone application, via a physical, on-device button, and or via a wirelessly connected smart bottle that tracks fluid intake provides inputs to the total hydration deficit, wherein the deficit is determined as sweat volume and electrolyte loss minus water and electrolyte consumed. The mobile app on a smart device may have a status indicator to indicate the user's hydration deficit level in a color-coded manner with text that indicates whether the user's status is OK, at risk, or dehydrated.

Figure 24B:
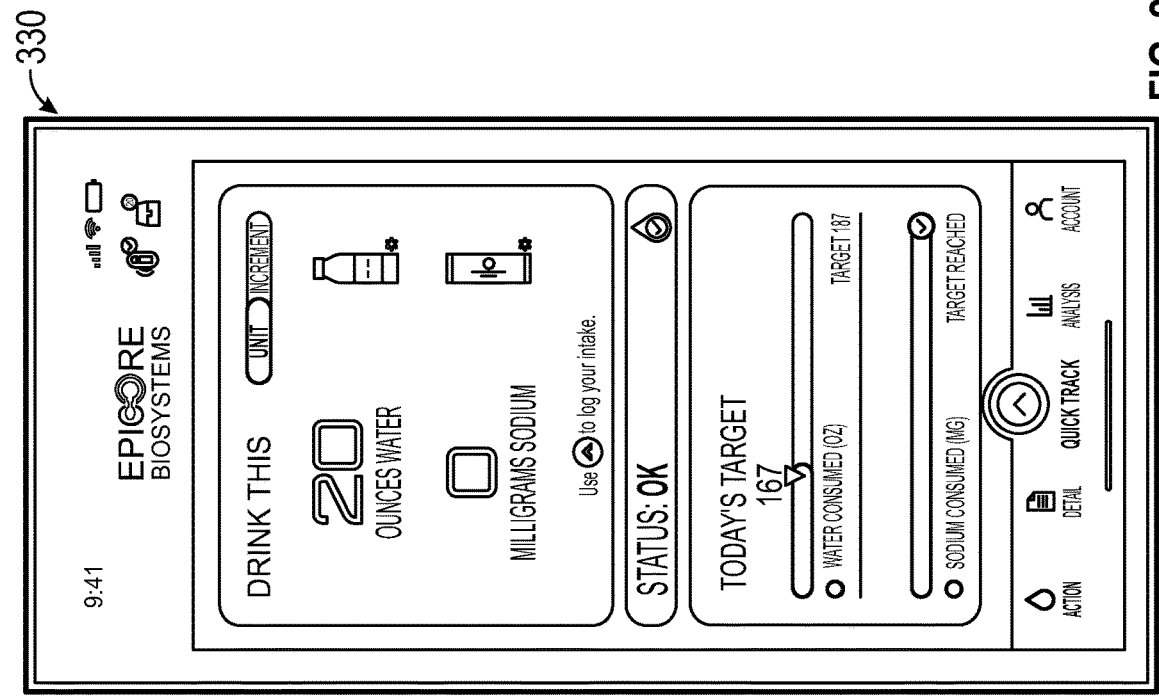
FIG. 24B is a plan view of a second example of a smartphone app graphic user interface showing an OK user status.
Figure 24A:
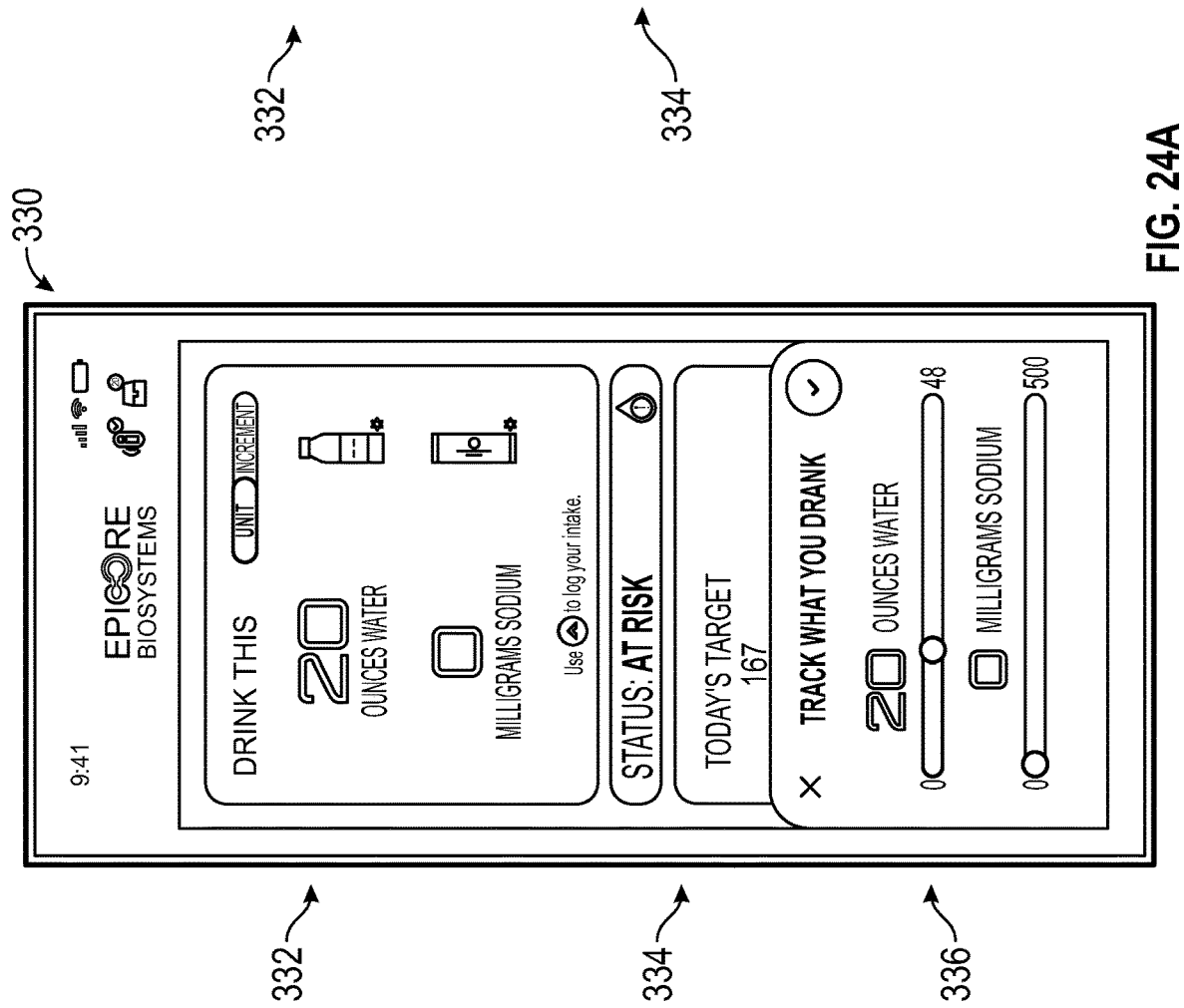
FIG. 24A is a plan view of a first example of a smartphone app graphic user interface showing an At Risk user status.

For example, referring to FIGS. 24A and 24B, two views of a smartphone app graphic user interface (GUI) are shown at 330. In FIG. 24A, a first portion of the GUI, shown at 332, displays a recommended volume of water and electrolytes needed for the user to rehydrate. A second portion of the GUI, shown at 334, displays a status level that can vary from OK to at risk to dehydrated. Advantageously, the status level display may be color coded for easy recognition by the user. When needed, the user may open a tray, shown at 336, that may be used to input the amount of fluid, such as water, consumed.

FIG. 24B is similar to FIG. 24A, and shows the first portion 332 of the GUI 330, and an alternate version of the second portion 334 indicating a user status of OK. The tray 336 is not shown in FIG. 24B.

An athlete may, for example, wear the wearable biofluid volume and composition system 10 on the bicep muscle group. Sweat profile data including the wearer's height, weight, and gender may be entered into the smartphone software application with the exercise or work being executed. Real-time sweat profile data is then captured on the smartphone and may be streamed to connected exercise equipment, including, but not limited to, treadmills, ellipticals, stationary bicycles, and other smart fitness equipment, via a wireless connection, such as Bluetooth, ANT+, a cellular connection, using an application programming interface (API). The athlete may then view the real time sweat profile data on their smartphone, smartwatch, and/or on the user interface display of the smart fitness equipment in real-time.

Advantageously, the collected sweat data can be summarized after work, exercise, or a rehabilitation routine, and delivered to the wearer, work manager, or caregiver. This summary sweat data may then provide actionable feedback in the form of hydration recommendations, for example fluid, metabolites, and electrolytes, and nutrition recommendations, for example, dietary food intake, based on a loss of nutrients in sweat.

Further, data may also be transmitted to the centralized servers from the smartphone or smartwatch for long term storage of data across multiple sessions, and longitudinal analysis, including analysis using machine learning and artificial intelligence tools.

Figure 25:
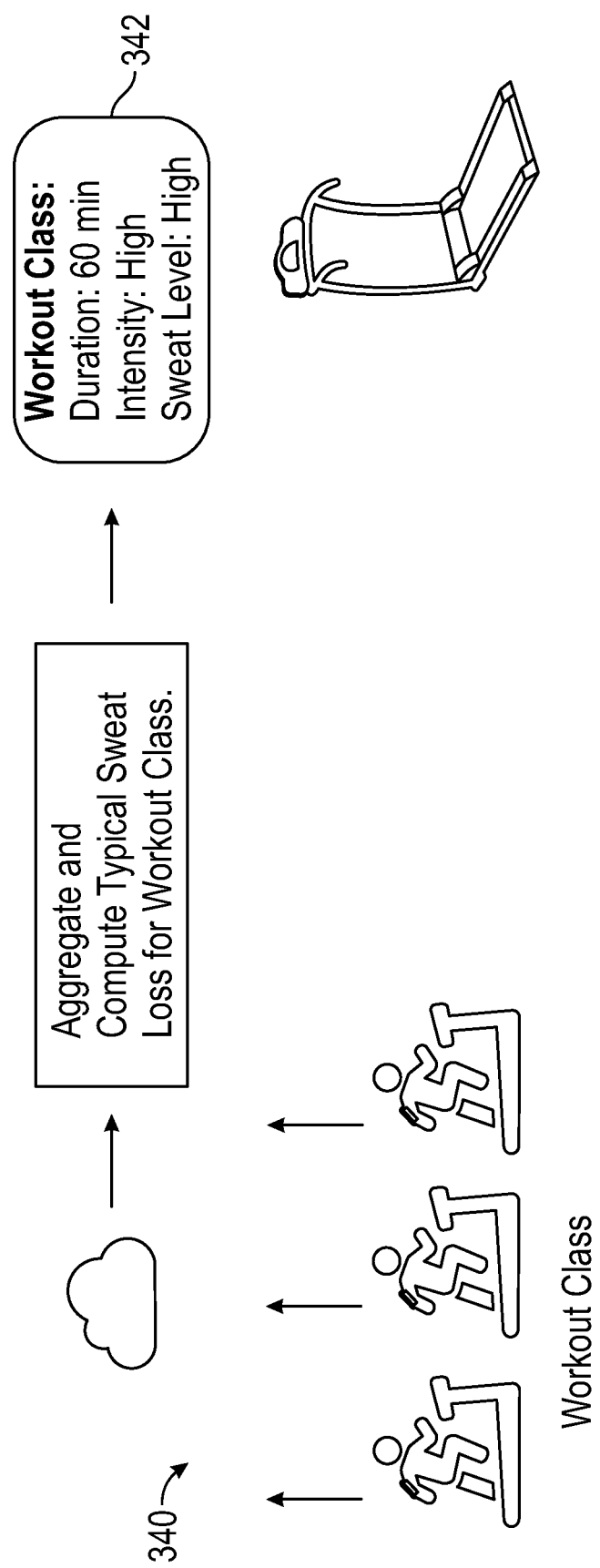
FIG. 25 is a schematic illustration of one example of the flow of aggregate sweat data from a group of users to an end user of the collected aggregate sweat data.

As shown in FIG. 25, sweat data aggregated from multiple athletes or participants in a defined fitness activity, such as, but not limited to, an aerobics class or cross-training 340, may be used to assess an average or a weighted sweat rate for the physical activity. The average, weighted, or predicted user-specific sweat rate may then be provided to potential future participants in the fitness activity as an indicator of an expected sweat rate for the potential participant when participating in the fitness activity. This sweat rate may be displayed on a smartphone, other smart device, or on exercise equipment, such as shown at 342 in FIG. 25. Thus, typical sweat loss data may be shown in an exercise class description for users who want to know how much sweat loss occurs in the exercise class.

Figures 9, 9A:
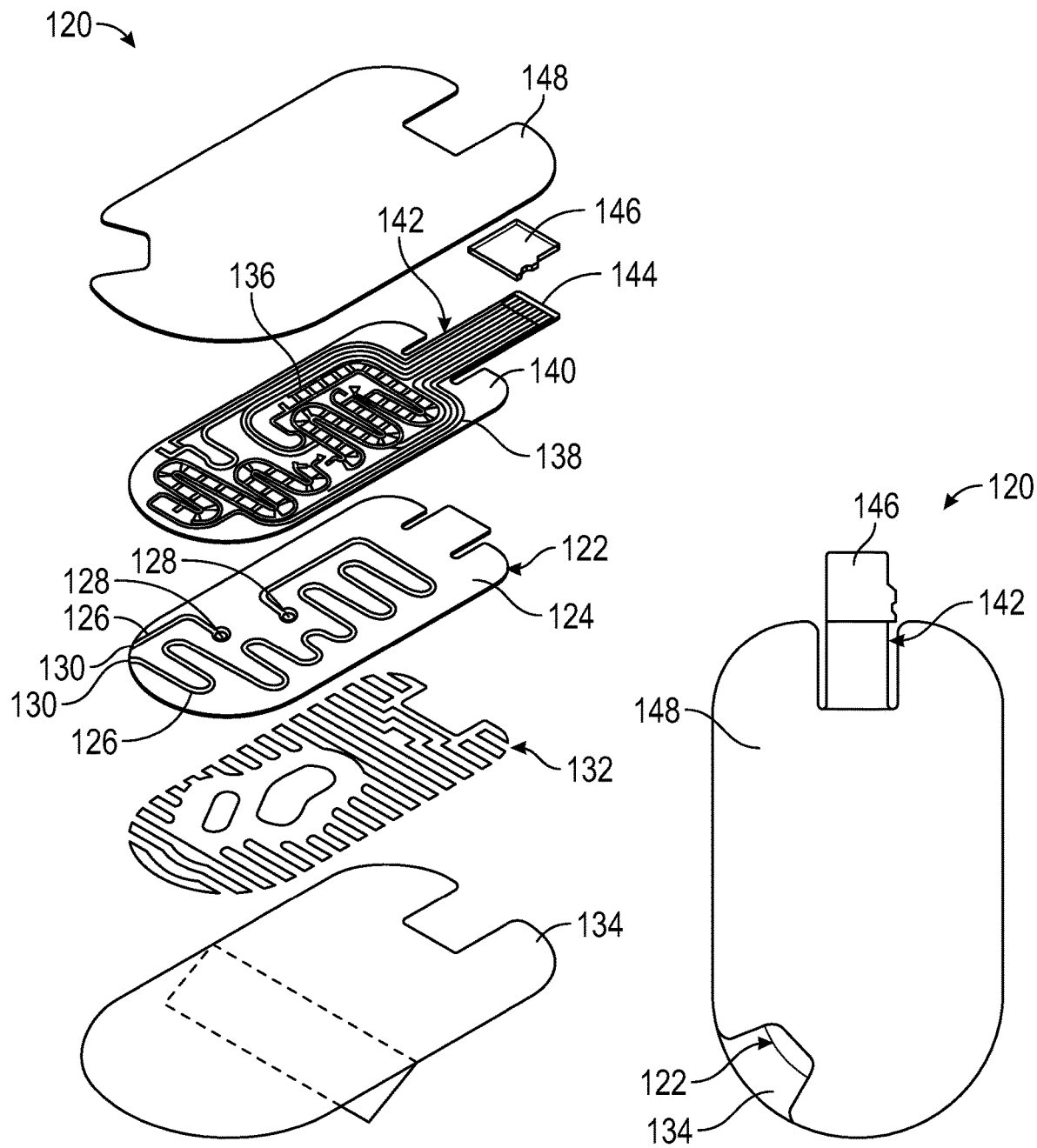
FIG. 9 is an exploded view of a third embodiment of the flexible fluid capture substrate illustrated in FIGS. 1, 1A, 2, and 6.
FIG. 9A is a top plan view of the flexible fluid capture substrate illustrated in FIG. 9 shown assembled.

Referring now to FIGS. 9 and 9A, a third embodiment of the flexible fluid capture substrate is shown assembled at 120 in FIG. 9A and exploded in FIG. 9. The flexible fluid capture substrate 120 is similar to the flexible fluid capture substrates 14 and 92 and is also configured to be worn on a human body. The flexible fluid capture substrate 120 includes a flexible substrate body 122 having a first, outwardly facing surface 124, a second, skin-facing surface (not shown), and one or more sweat collection or microfluidic channels 126 formed in the flexible substrate body 122. Each microfluidic channel 126 has a first end defining a sweat inlet port 128, and a second end defining a sweat outlet port 130. The skin-facing surface (not shown) includes an adhesive, such as the patterned or striated adhesive 132, that bonds to skin of the wearer, and may be covered by a removable adhesive liner 134 formed from any desired flexible material, such as for example as air/oxygen impermeable material. The striated adhesive 132 also defines fluidic channels that prevent sweat from building up underneath the flexible fluid capture substrate 120.

Electrodes 136 and one or more electrical traces 138 may be printed on either side of a flexible substrate layer 140, formed from a desired flexible material, including but not limited to silicone, clear polyester, PET, and TPU, as described in detail above. A ribbon cable 142 extends longitudinally outward from one end of the flexible substrate layer 140 and is formed from the same material as the flexible substrate layer 140. Portions of the traces 138 are formed on the ribbon cable 142. Distal ends of the traces 138 in the ribbon cable 142 are exposed and define conductive connector pads 144. The flexible substrate layer 140 is attached to the flexible substrate body 122. The ribbon cable 142 may include a microSD® connector 40 as shown in FIG. 6. Alternatively, the ribbon cable 142 may include other connectors, including but not limited to a zero insertion force (ZIF) style connector, a perpendicular style connection formed from conductive micro hook and loop, or electrically conductive adhesive transfer tape, such as z-axis conductive tape. When the ribbon cable 142 includes the microSD® connector 40, a distal end of the ribbon cable 142 may include the stiffener 146 and may also include the gasket 44 configured to mate with the microSD® socket 24.

The flexible fluid capture substrate 120 also includes an upper layer defining a skirt 148. The skirt 148 is formed from a flexible, soft material that may be softer and larger than the flexible substrate body 122 and the flexible substrate layer 140, such that peripheral edges of the skirt 148 extend outwardly beyond a peripheral edge of the flexible substrate body 122 and therefore contacts the skin of the wearer. The portion of the skirt 148 that contacts the skin of the wearer may also include an adhesive and thus adhere to skin. The skirt 148 provides a mechanical transition between the mechanical modulus of skin and the modulus of the flexible fluid capture substrate 120. By smoothening the transition between the modulus of skin and modulus of the flexible fluid capture substrate 120, the peripheral edges of the flexible fluid capture substrate 120 are better adhered to the skin. The skirt 148 may be formed from any desired flexible, soft material, such as for example medical or kinesiology tape.

Figure 10:
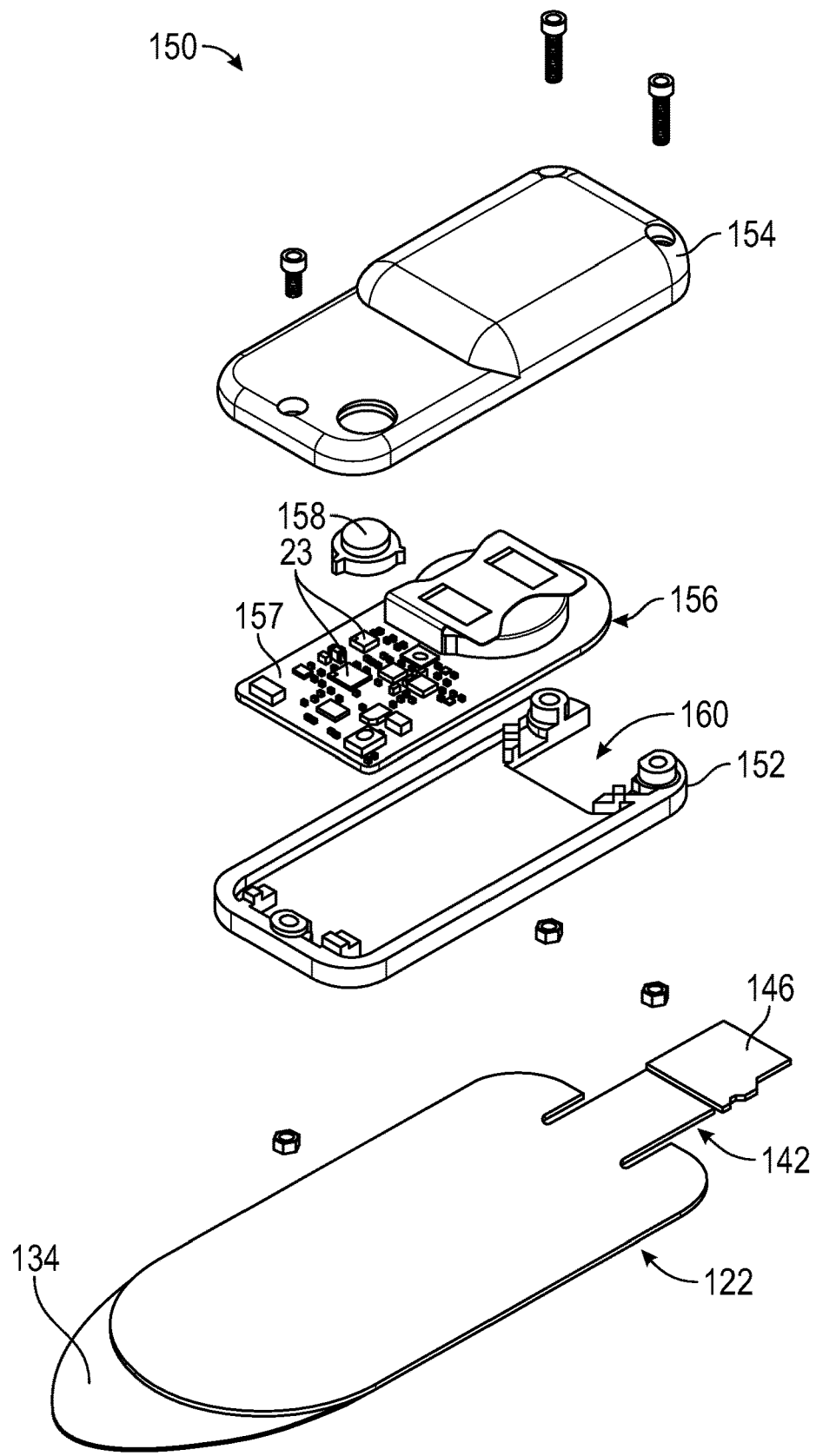
FIG. 10 is an exploded view of a second embodiment of the electronic module illustrated in FIGS. 1, 1A, and 2 shown with the flexible fluid capture substrate illustrated in FIG. 9.

Referring now to FIG. 10, an exploded view of a second embodiment of the electronic module illustrated in FIGS. 1, 1A, and 2 is shown at 150 with the flexible fluid capture substrate 120 (with the flexible substrate layer 140 attached thereto, and with an alternate embodiment of the removable adhesive liner 134) illustrated in FIGS. 9 and 9A. The electronic module 150 is similar to the electronic module 12 and includes a base 152, a cover 154, and PCB assembly 156 mounted within the electronic module 150. The base 152 and the cover 154 may be formed from any desired rigid plastic material, such as acrylonitrile butadiene styrene (ABS). Alternatively, the base 152 and/or the cover 154 may be formed for any other rigid plastic material such as polypropylene, and may be formed from opaque, semi-transparent material, or transparent material. Additionally, the base 152 and cover 154 may be relatively thin, such as having a thickness within the range of about 1 mm to about 2 mm. Like the electronic module 12, the electronic module 150 is designed to be disposable or reusable.

The PCB assembly 156 includes a PCB 157, a microcontroller and other required functional electronic components 23, described above, mounted to the PCB 157 and necessary to operate the electronic module 150. The PCB assembly 156 includes an on/off button 158 and an electrical socket 160 formed in a first distal end of the electronic module 150. Like the electrical socket 24, the electrical socket 160 may be a microSD® socket. Alternatively, the electrical socket 160 may be any desired conventional electrical socket.

Figure 11:
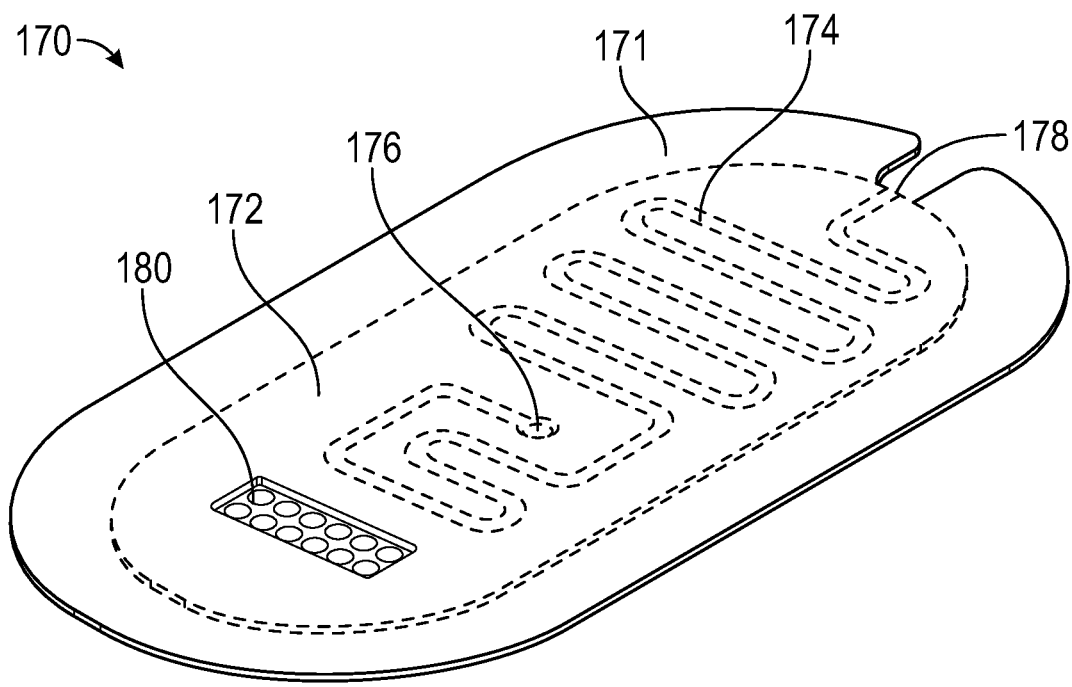
FIG. 11 is a perspective view of a fourth embodiment of the flexible fluid capture substrate illustrated in FIGS. 1, 1A, 2, and 6.

Referring now to FIG. 11, a portion of a fourth embodiment of the flexible fluid capture substrate is shown at 170. The flexible fluid capture substrate 170 is similar to the flexible fluid capture substrate 120 and is also configured to be worn on a human body. The flexible fluid capture substrate 170 includes a flexible substrate body 172 having one or more sweat collection or microfluidic channels 174 formed in the flexible substrate body 172. Each microfluidic channel 174 has a first end defining a sweat inlet port 176, and a second end defining a sweat outlet port 178. The skin-facing surface includes an adhesive (not shown).

Figure 12:
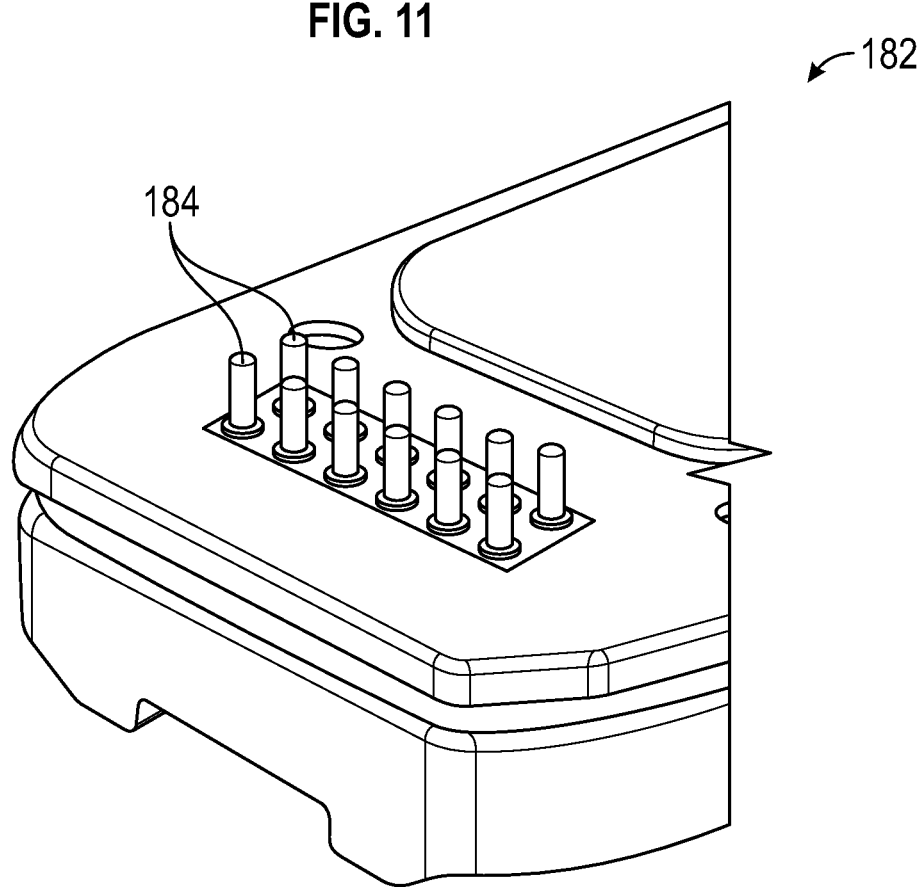
FIG. 12 is a perspective view of a portion of a third embodiment of the electronic module illustrated in FIGS. 1, 1A, and 2 showing the electrical connection pins.

Electrodes and one or more electrical traces (not shown) may be printed on either side of a flexible substrate body 172. The flexible fluid capture substrate 170 includes a skirt 171 and an electrical connector pad 180 configured to contact electrical connection pins 184 in an associated electronic module 182, a portion of which is shown in FIG. 12. Unlike the electronic module 150, the electronic module 182 does not include the electrical socket 160, and the flexible fluid capture substrate 170 does not include the ribbon cable 142. Rather, the electronic module 182 includes the electrical connection pins 184 extending from a skin-facing surface thereof. The electrical connection pins 184 may be spring biased.

The embodiments of the invention described above refer to a wearable biofluid volume and composition system 10, that is comprised of the electronic module 12 and the complimentary, disposable, one-time use, electrode or electrochemical sensor array embedded into the flexible fluid capture substrate 14. Alternatively, an electrochemical sensor array may be embedded in a moisture absorbent material, described below.

Figure 13:
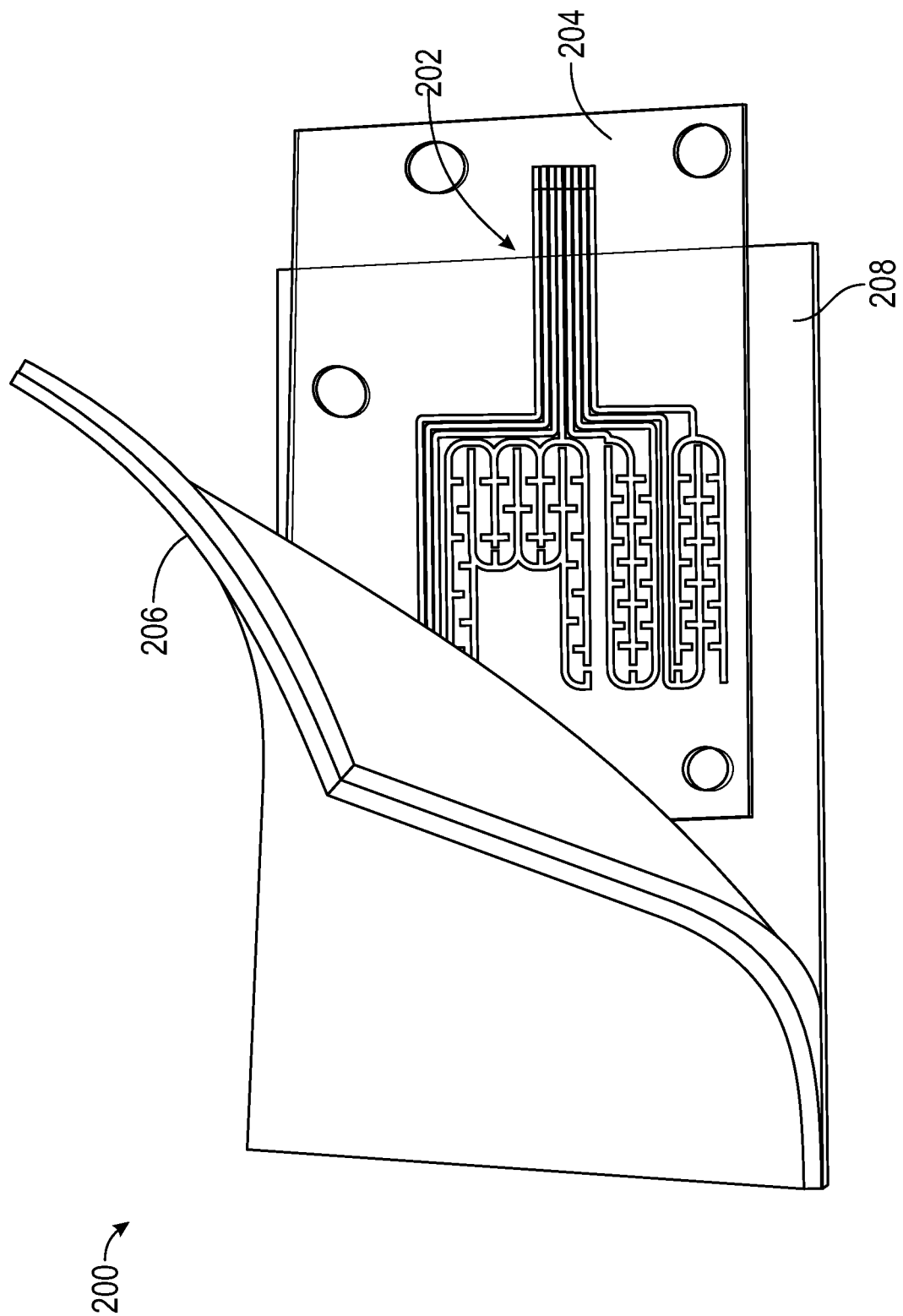
FIG. 13 is a plan view of one embodiment of a wound care dressing having the electrode array and traces according to this invention formed on a clear substrate and showing an outer layer partially peeled back for clarity.

FIG. 13 is a plan view of one embodiment of a moisture absorbent material configured as a wound care dressing 200. The wound care dressing 200 includes a disposable electrode array 202 formed on a clear substrate 204 and positioned between an inner fibrous wicking layer 206 and an outer vapor and/or water barrier 208, such may be found in a conventional wound care dressing, a face mask, or diaper pad. In FIG. 13, the inner fibrous wicking layer 206 is shown partially peeled back for clarity. Thus, although the embodiment of the invention shown at 200 is described in the context of a wound care dressing, it will be understood that the same structure may be used in the construction or manufacture of a face mask or a diaper pad. The electrode array 202 is similar to any of the electrode arrays or the combinations of electric traces and electrodes described herein.

In use, the inner fibrous wicking layer 206 is placed closest to the skin of the wearer. Thus, in contrast to the flexible fluid capture substrates 14, 92, 120, and 170 described above, fluid will not fill an empty fluid channel, but will fill, i.e., be absorbed by the inner fibrous wicking layer 206. The inner fibrous wicking layer 206 may be formed from any desired wicking material, including but not limited to cotton, polyester, nylon, cellulose, calcium-alginate, alginate, calcium-sodium-collagen alginate, hydrogel, hydrocolloids, sodium polyacrylate, polyacrylate absorbents, foam, and any composites of materials including but not limited to materials listed herein. As the inner fibrous wicking layer 206 fills with fluid and the moisture from the absorbed fluid reaches the electrode array 202, the impedance between the electrodes in the electrode array 202 changes. Diapers and diaper pads for example, are designed to wick urine away from the skin. Wound dressings and face masks are designed to behave similarly. As the moisture within the fibrous wicking layer 206 reaches the outer barrier 208, against which the clear substrate 204 and its electrode array 202 are positioned, the electronic module (not shown in FIG. 13) computes the change in resistance and can estimate moisture levels.

Figure 14A:
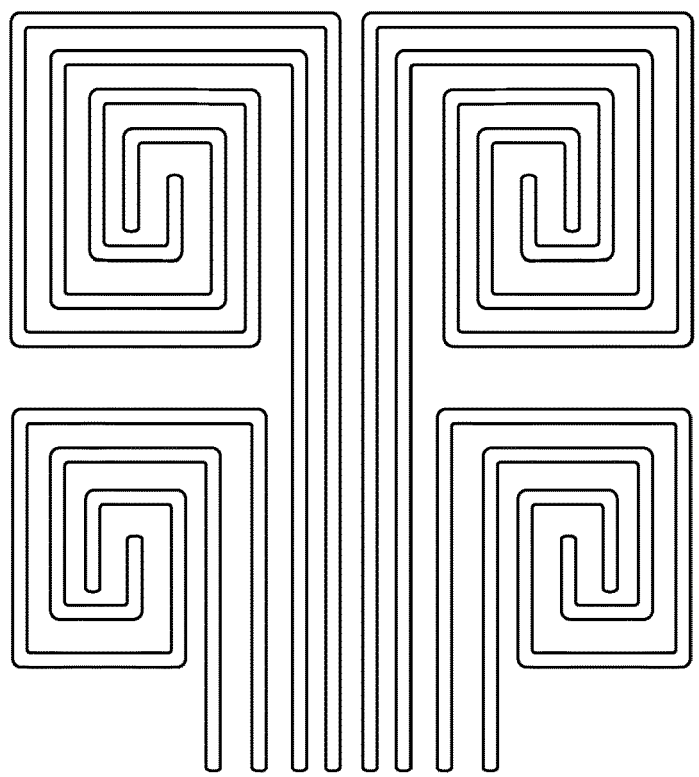
FIG. 14A is a first alternate embodiment of a trace and electrode array.
Figure 14B:
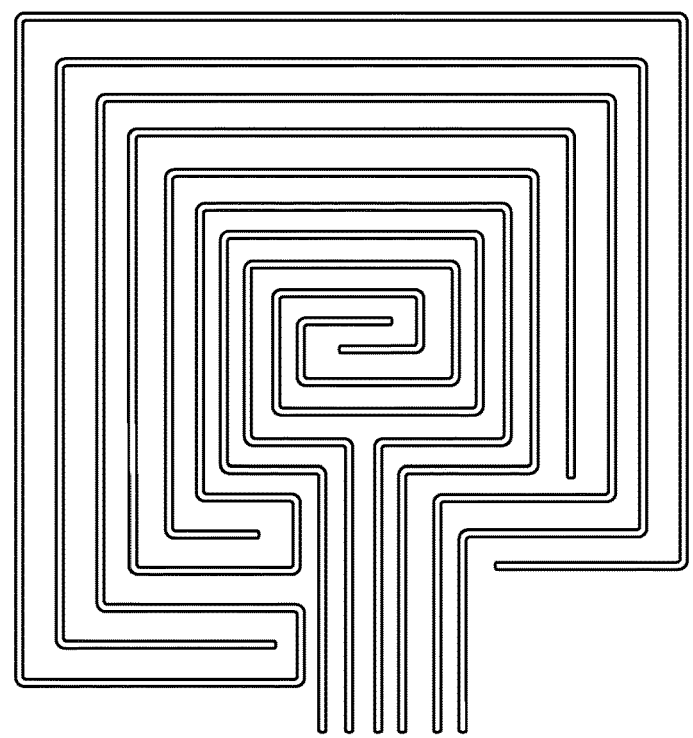
FIG. 14B is a second alternate embodiment of a trace and electrode array.
Figure 15C:
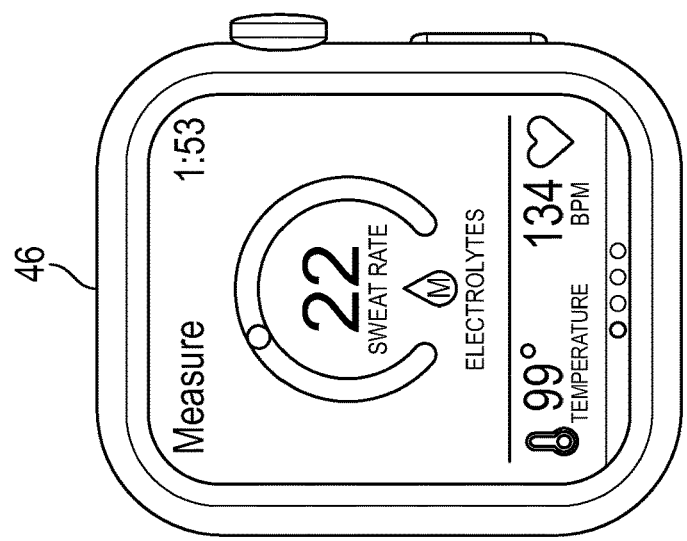
FIGS. 15A through 15F are examples of smart watch face displays associated with use of the embodiments of the continuous wearable biofluid volume and composition system according to this invention.
Figure 15B:
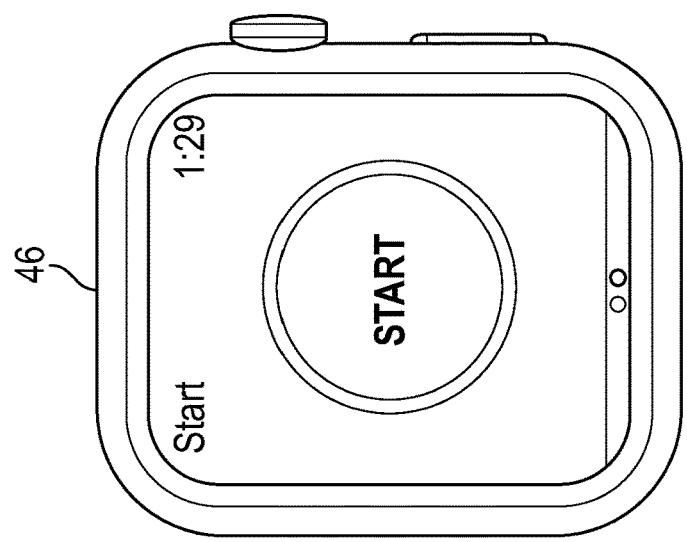
Figure 15A:
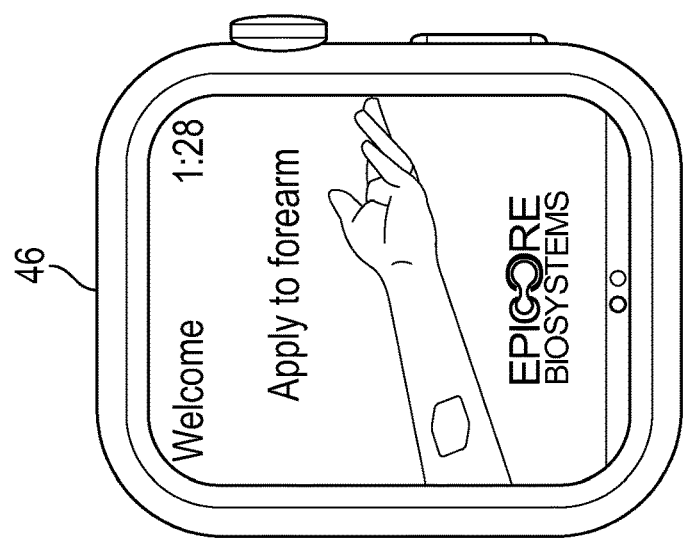
Figure 15F:
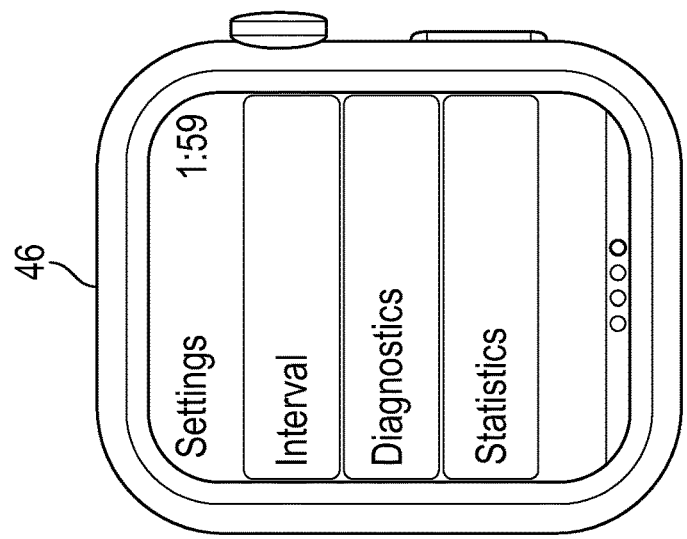
Figure 15E:
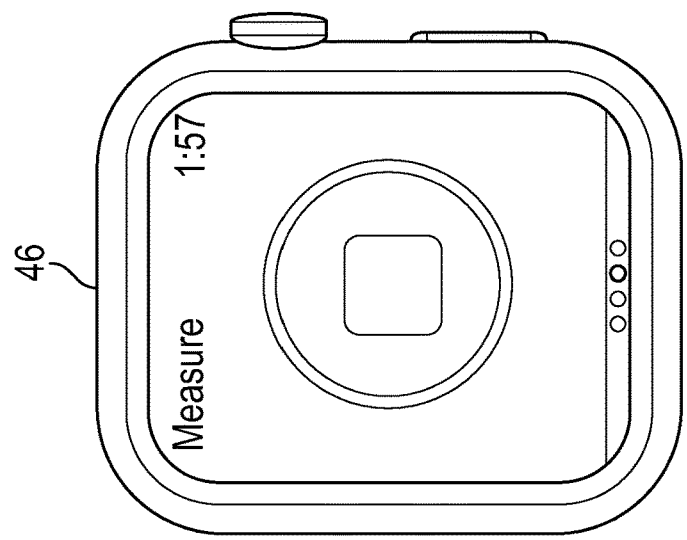
Figure 15D:
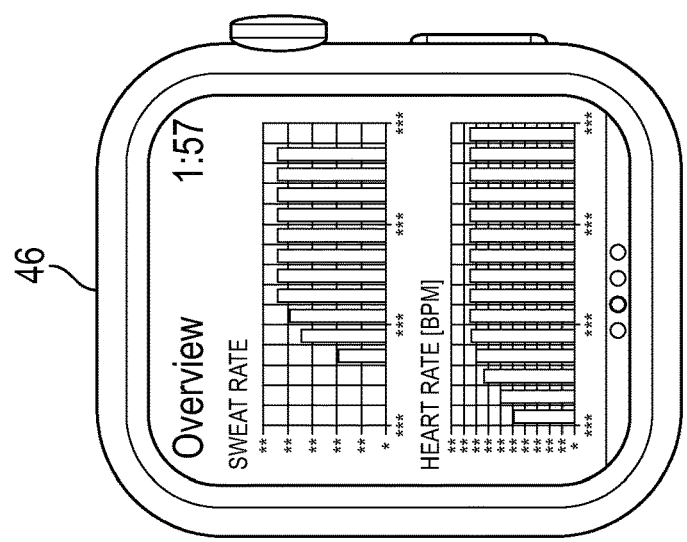

The electrode array 202 may be designed in geometries that aid in distinguishing locations of moisture spread. In FIG. 6, the electrode array, i.e., the electrodes 35 and the trace 36, forms several regions, for example R1 through R3, and each region may be measured separately. The change in value across geographical regions R1 through R3 can indicate the spread of moisture and can provide an indication of efficacy of a moisture absorbing product such as wound dressing, incontinence pad, or a face mask, and also aid in determining when the product should be replaced with a fresh, dry one. For example, the electrodes may reside in quadrants or tiles following Cartesian coordinates, such as at 210 in FIG. 14A. As moisture spreads, electrodes in additional regions or quadrants may be configured to sense a change in impedance. If the fibrous wicking layer 206 is designed with a central wicking location, for example in a wound dressing, then electrodes following polar coordinates, such as at 212 in FIG. 14B, may add insight as to which ring region experiences an impedance change as moisture spreads from the center outward in successive rings over time. For example, a smartphone or a smart watch may display the real-time sinusoid signal measured on electrode region 3 under the moisture wicking material.

The healing response requires a proper balance of moisture, pH, and temperature levels. Wound healing may be delayed if the wound becomes too dry, and excessive fluid retention at the wound surface may also result in poor healing and maceration of tissue. Advantageously, real-time monitoring of wound moisture with notification alarms and/or alerts is thus critical as a way to enable caretakers to be informed about wound dressing viability and to optimize healing.

If desired, the disposable, one-time-use, flexible fluid capture substrates 14, 92, 120, and 170, and electrodes, including the electrode pads 35, 35A, 35B, 106, and 136, and the electrode array 202 may contain assays, such as electrochemical assays, enzymatic assays, or aptamer-based assays, that create a voltage due to an electrochemical reaction with fluid that may be measured by the electronic module using a potentiostat circuit.

Figure 16:
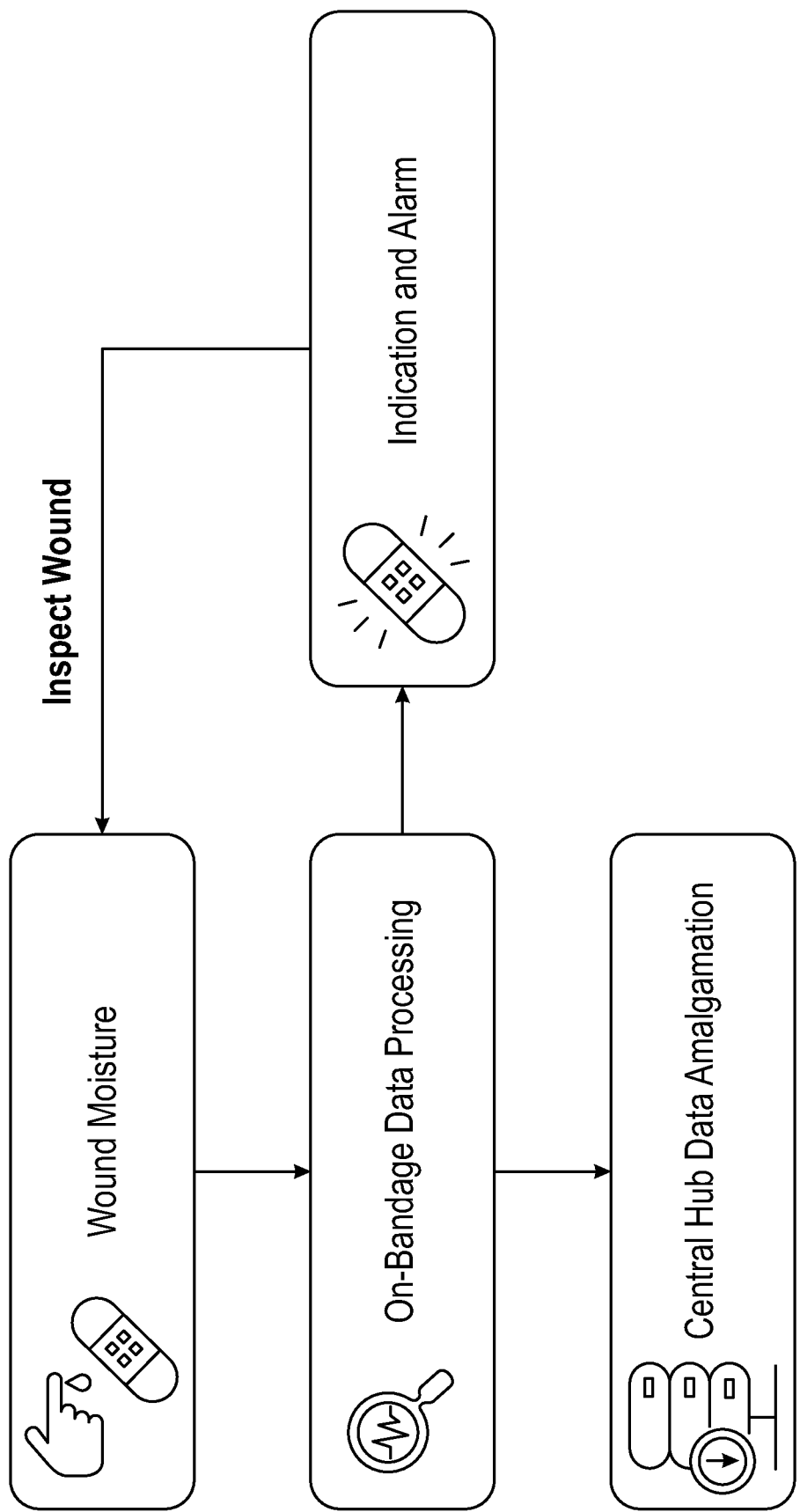
FIG. 16 is a flow chart showing one example of wound exudate moisture measurement data flow.
Figure 17:
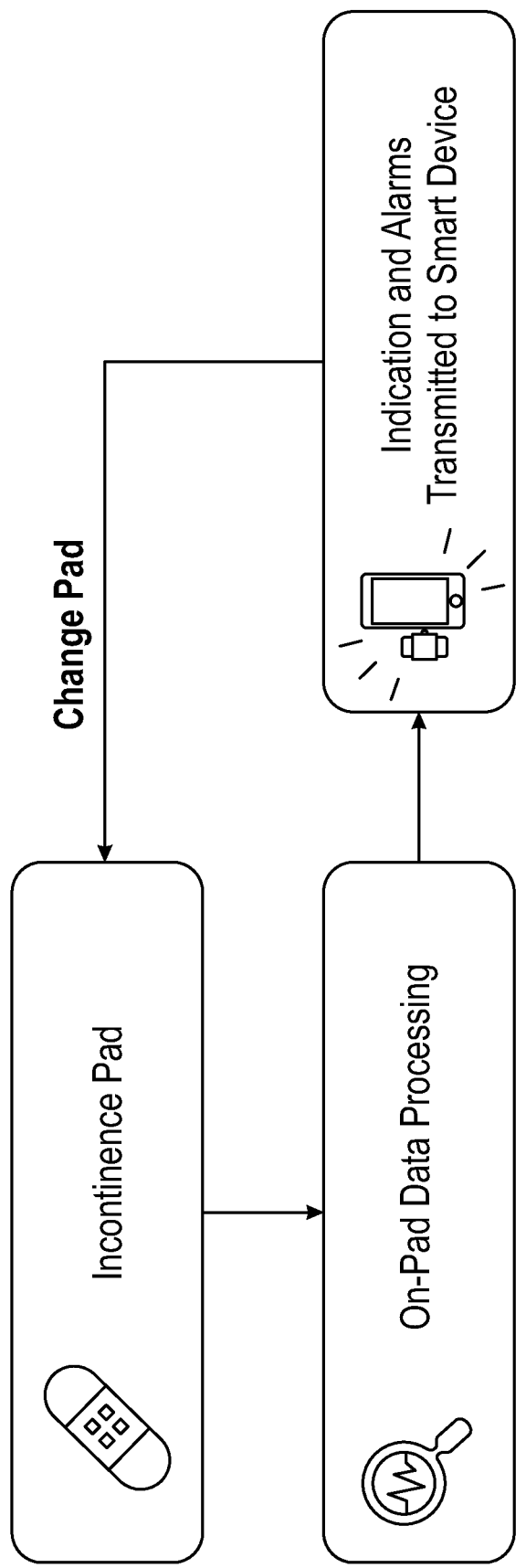
FIG. 17 is a flow chart showing one example of incontinence moisture measurement data flow.

The measurements taken and displayed by the embodiments of the wearable biofluid volume and composition systems described herein, such as the wearable biofluid volume and composition system 10, may be used to alert the user and/or provide information to a third party to take a course of action such as change a wound dressing or an incontinence pad, or rehydrate with a specific amount of electrolytes or a specific volume of fluid (see FIGS. 16 and 17). The measurements may also be used in computations wherein they are compared against regional or institutional safety thresholds that would trigger an incident report and should be logged.

Additionally, the embodiments of the wearable biofluid volume and composition systems described herein, such as the wearable biofluid volume and composition system 10, may be used to detect biomarkers in exudate that promote wound healing, such as FALL39 and Thymosin β-4.

When the moisture absorbent material is configured as an incontinence pad 200, fluid fill in the incontinence pad 200 may be monitored. A wirelessly transmitted alert or notification to a smartphone or a smart watch can alert the wearer, a caregiver, or another associated party as to how much estimated volume is left until the incontinence pad 200 is full and also when the incontinence pad 200 is full.

It is also known that mask efficacy in, for example, N95 masks, falls as the mask filter becomes wet. The embodiments of the wearable biofluid volume and composition systems described herein, such as the wearable biofluid volume and composition system 10, and the moisture absorbent material 200 shown in FIG. 13, may be used to monitor the area of the mask that becomes wet and to alert the user as when to change the mask.

In some embodiments of the wearable biofluid volume and composition system 10, a temperature sensor may be incorporated into the flexible fluid capture substrate 14, 92, 120, and 170 by applying positive temperature coefficient (PTC) ink in a manner similar to the way in which Ag and Ag/AgCl inks are used to create the trace 36. An electric current that runs through the PTC ink can measure a temperature of the fluid on the flexible fluid capture substrate 14, 92, 120, and 170.

Figure 18:
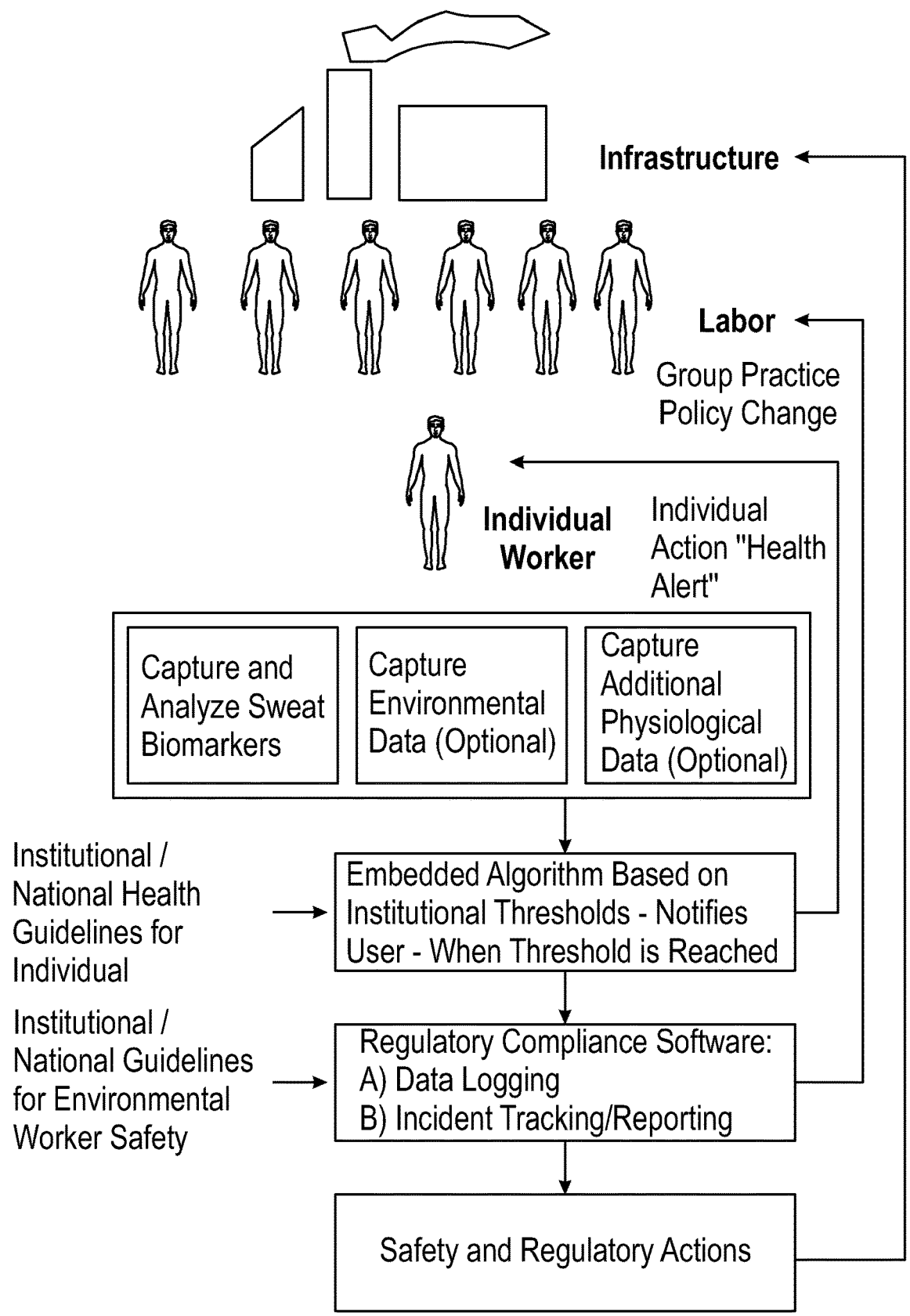
FIG. 18 is a flow chart showing one example of worker safety data flow and associated suggested courses of action.
Figure 19:
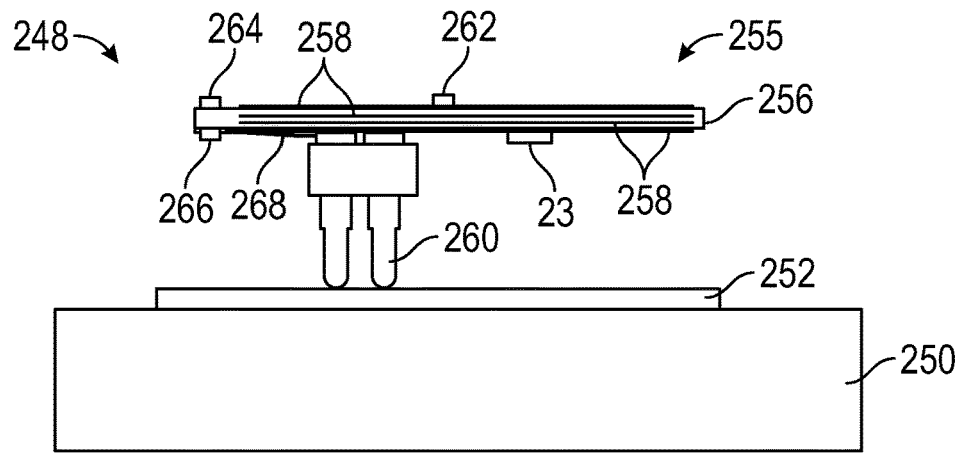
FIG. 19 is a first schematic side elevational view of an alternate embodiment of the continuous wearable biofluid volume and composition system illustrated in FIGS. 1, 1A, and 2, showing the spring biased electrical connection pins making contact with the microfluidic flexible fluid capture substrate.

In addition to local wirelessly networked computers, including smart watches and smartphones, a central server or data repository may receive biometric data inputs for incident reporting for regulatory compliance or other purposes. The server software may also run statistical analysis over time to track dehydration and environmental parameters collected from the sweat monitoring device, i.e., the wearable biofluid volume and composition system 10. Workload changes and infrastructure changes can be extrapolated from the sweat and local wirelessly networked computer data across different work areas and worker tasks, as shown in FIG. 18. The results obtained may be used to drive labor policy changes and for capital or infrastructure changes for the institution, as shown in FIG. 18. Biometric threshold values determined by national and industry safety boards may be set, and if exceeded, an alert/notification may be given to the individual to replenish fluids or take a break.

Referring now to FIGS. 19 through 22, a second embodiment of the continuous wearable biofluid volume and composition system is shown schematically at 248 attached to a user's body, such as to the user's forearm or bicep 250. The continuous wearable biofluid volume and composition system 248 includes a microfluidic flexible fluid capture substrate 252, similar to the microfluidic flexible fluid capture substrate 14, and an electronic module 254. The electronic module 254 includes a cover 254A, a base 254B, and a PCB assembly 255 having a PCB 256. The illustrated PCB 256 may be formed from any desired material, such as glass-reinforced epoxy laminate material, such as FR4. FR4 has a thermal conductivity of about 0.25 W/mK, thus making it a good thermal insulator.

The illustrated PCB 256 includes a plurality of copper planes 258, a microcontroller and other required functional electronic components 23, described in detail above, electrical connection pins 260, a DC-DC boost converter 262 that boosts the voltage from the battery to a fixed DC voltage level, a first temperature sensor 264, and a second temperature sensor 266. The illustrated electrical connection pins 260 are similar to the electrical connection pins 184, extend from a skin-facing surface of the PCB 256, may be spring biased, and are configured to contact an electrical connector pad (not shown) on the microfluidic flexible fluid capture substrate 252.

The first temperature sensor 264 is mounted to the PCB 256 side facing the personal protective equipment (PPE) of the wearer, such as work coveralls (not shown). The second temperature sensor 266 is mounted opposite the first temperature sensor 264 on a skin-facing side of the PCB 256. The material of the PCB 256 provides thermal insulation between the first temperature sensor 264 and the second temperature sensor 266.

The embodiment of the continuous wearable biofluid volume and composition system 248 may be used to measure a temperature gradient. For example, a temperature difference measured between the first and the second temperature sensors 264 and 266 provides a temperature gradient measurement wherein the direction and magnitude of heat radiated may be determined. Heat may be radiated from the sun through the PPE to the non-skin side housing, i.e., the cover 254A, the non-skin side first temperature sensor 264, through the PCB 256, to the skin-side temperature sensor 266, to the skin-side housing, i.e., the base 254B, to the microfluidic flexible fluid capture substrate 252, and finally to the skin, such as the bicep 250.

Figure 20:
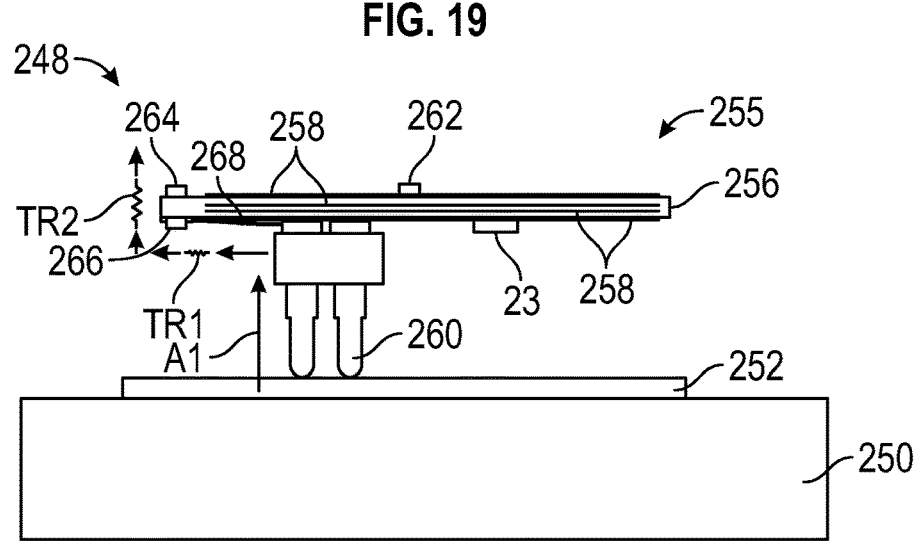
FIG. 20 is a second schematic side elevational view of the alternate embodiment of the continuous wearable biofluid volume and composition system illustrated in FIG. 19, showing the thermal resistance between the electrical connection pins and the first and second temperature sensors.
Figure 21:
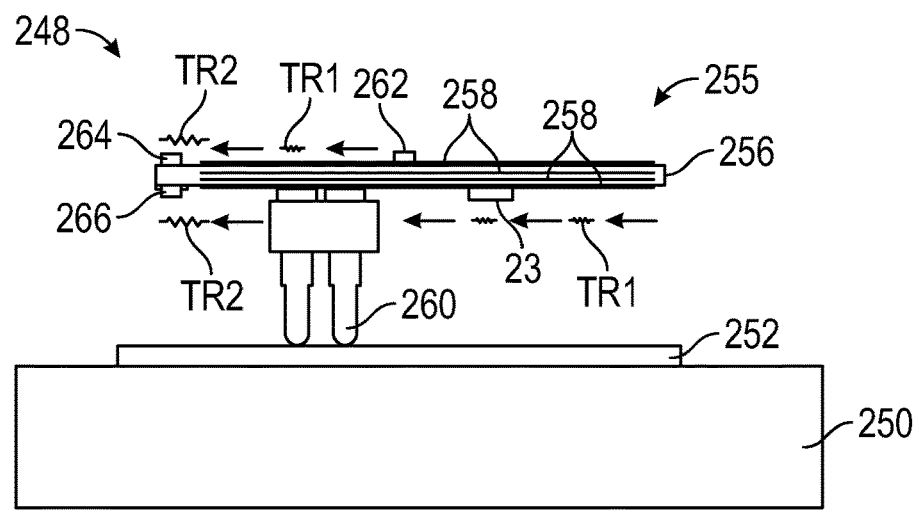
FIG. 21 is a third schematic side elevational view of the alternate embodiment of the continuous wearable biofluid volume and composition system illustrated in FIGS. 19 and 20, showing the thermal resistance between the first and second temperature sensors and other heat emitting electronic components on the printed circuit board.
Figure 22:
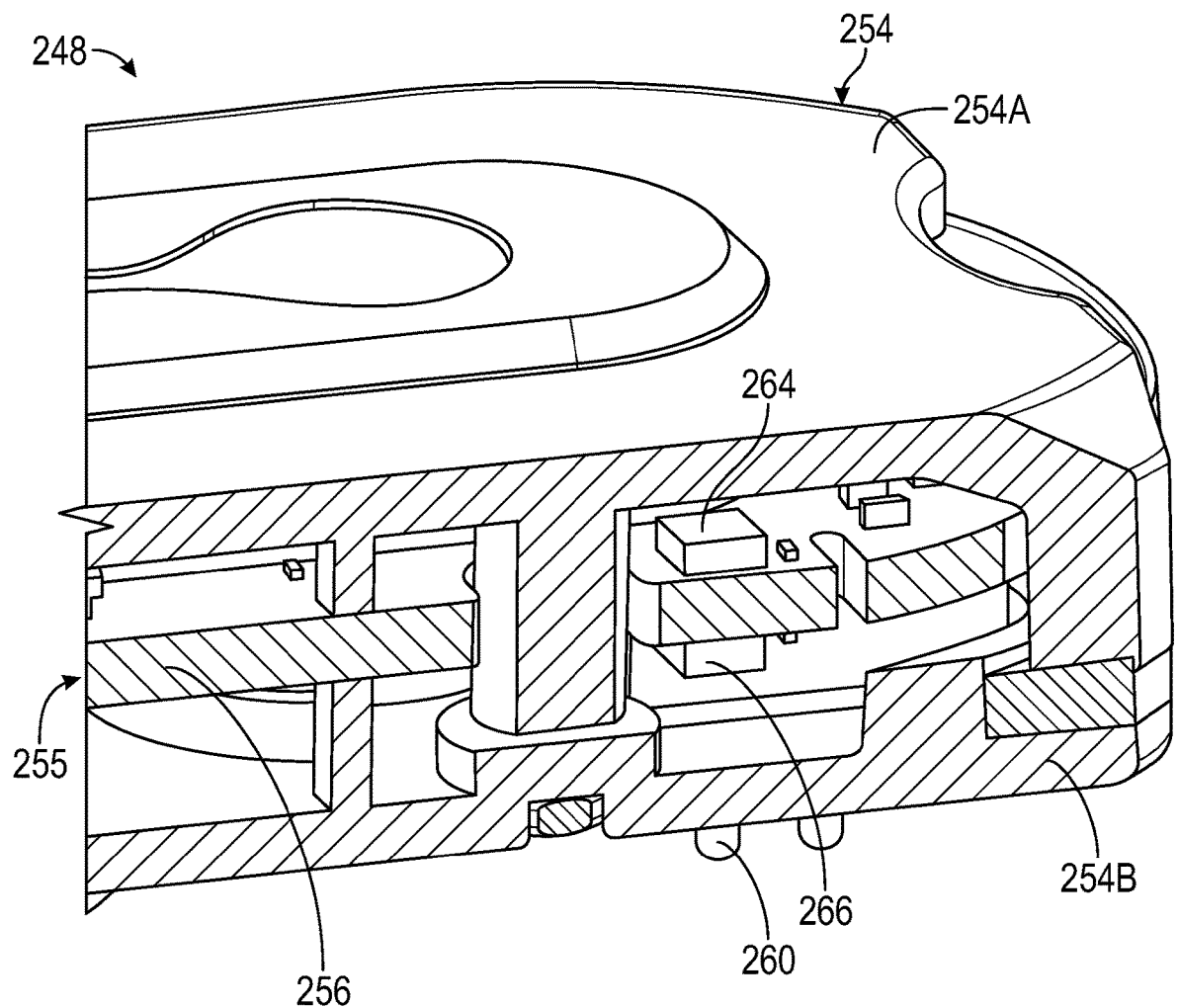
FIG. 22 is a side perspective view in cross-section of the alternate embodiment of the continuous wearable biofluid volume and composition system illustrated in FIGS. 19 through 21.

As shown in FIG. 20, the electrical connection pins 260 that make contact with the substrate 252 are spaced apart from the bicep 250 by the thickness of the substrate 252. The electrical connection pins 260 serve as a thermal conduit. A thermally conductive trace or pathway 268 is formed between the electrical connection pins 260 and the skin-side second temperature sensor 266. The thermally conductive material, such as copper, has a very high thermal conductivity coefficient of about 300 W/mK relative to the thermal conductivity coefficient of the FR4 material (about 0.25 W/mK) of the PCB 256. A portion of a copper plane 258 that is thermally conducting to the electrical connection pins 260 may be placed under and around the skin-side temperature sensor 266. As indicated by the arrow A1, heat from the skin (bicep 250) may flow of through the substrate 252 into the electrical connection pins 260, through the conductive pathway 268 formed between the electrical connection pins 260 and the skin-side second temperature sensor 266, and to the second temperature sensor 266.

The copper planes 258 that span the remainder of the PCB 256 do not extend to the first and the second temperature sensors 264 and 266, and thus define a space or moat around the first and the second temperature sensors 264 and 266. The thermal conductivity of the FR4 is relatively poor at about 0.25 W/mK, and as noted above, is a good thermal insulator. Thus, thermal conductivity of the FR4 provides a relatively large thermal resistance (see TR2) between the first temperature sensor 264 and the second temperature sensor 266

The second temperature sensor 266 is also in close proximity to the electrical connection pins 260, thereby reducing the distance between the second temperature sensor 266 and the thermal resistance, as shown at TR1. Active electrical components 23 that may generate heat are mounted further away from the temperature sensors 264 and 266, further increasing thermal resistance. Thus, heat from the electrical components 23 must travel a greater distance to the temperature sensors 264 and 266, therefore encountering increased resistance, as shown at TR1 in FIG. 21. The heat from the electrical components 23 must then travel across the moat around the first and the second temperature sensors 264 and 266, thus the moat provides a relatively large thermal resistance (see TR2).

In one embodiment of the continuous wearable biofluid volume and composition system 248, an electrical measurement of electrolytes may be taken in a separate fluidic channel of the substrate 252. The electrical measurement determines the conductivity of the sweat across an electrode pair having a known space between electrodes. The conductivity value is then used as a reference when computing the fluidic volume in another fluidic channel of the substrate 252 consisting of electrode pairs (see the descriptions of the embodiments illustrated in FIGS. 4A, 4B, 5A, and 5B.

Figure 23:
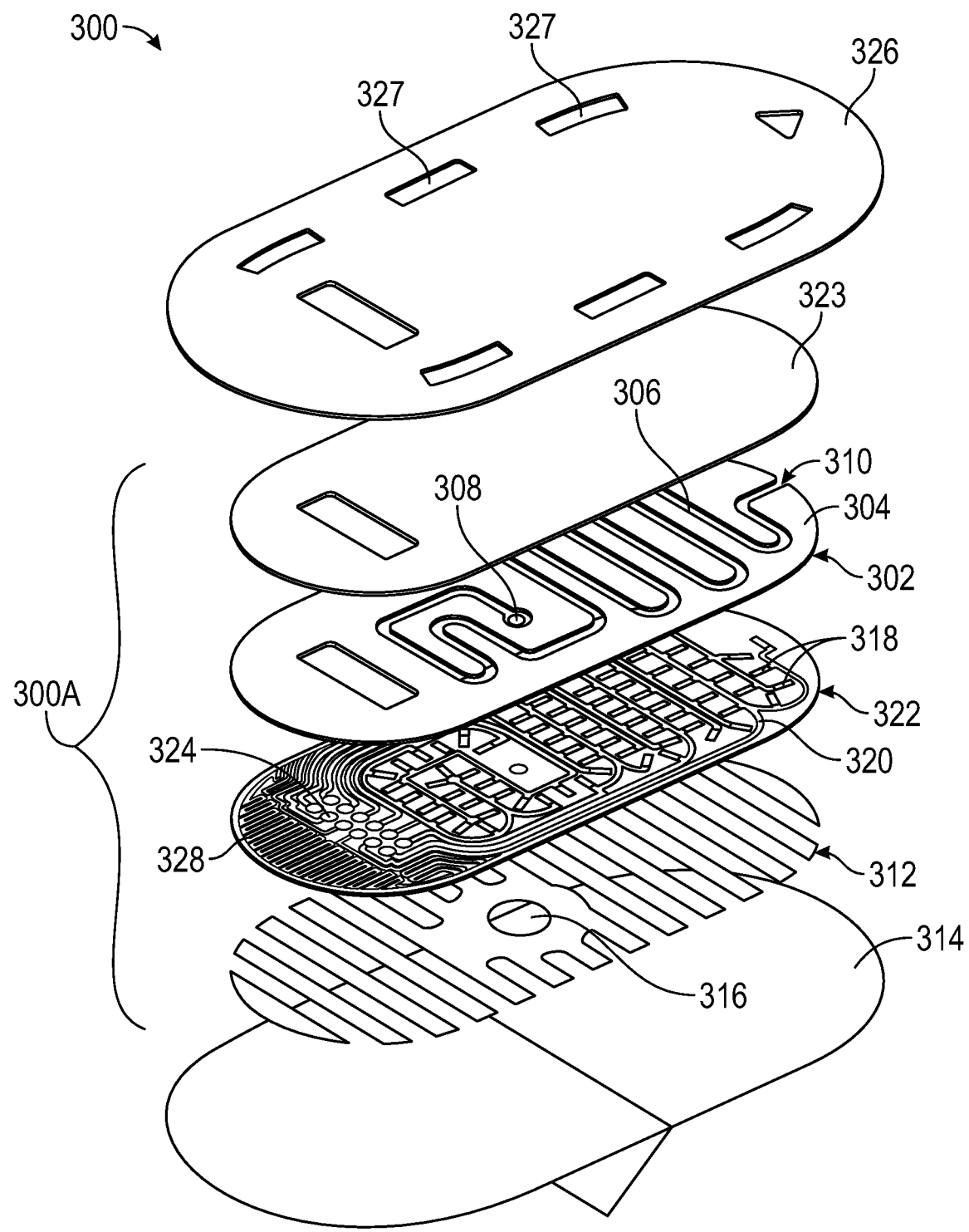
FIG. 23 is an exploded view of a fourth embodiment of the flexible fluid capture substrate illustrated in FIGS. 1, 1A, 2, 6, and 9.

In another embodiment of the continuous wearable biofluid volume and composition system 248, electrical measurements of electrolyte and volume, respectively, may be made in the same fluidic channel where the electrolyte measurement is performed with a first set of electrodes reserved for electrolyte measurement before the sweat proceeds through the channel and reaches a series of electrodes reserved for volume measurement (see for example FIG. 23).

Figure 23A:
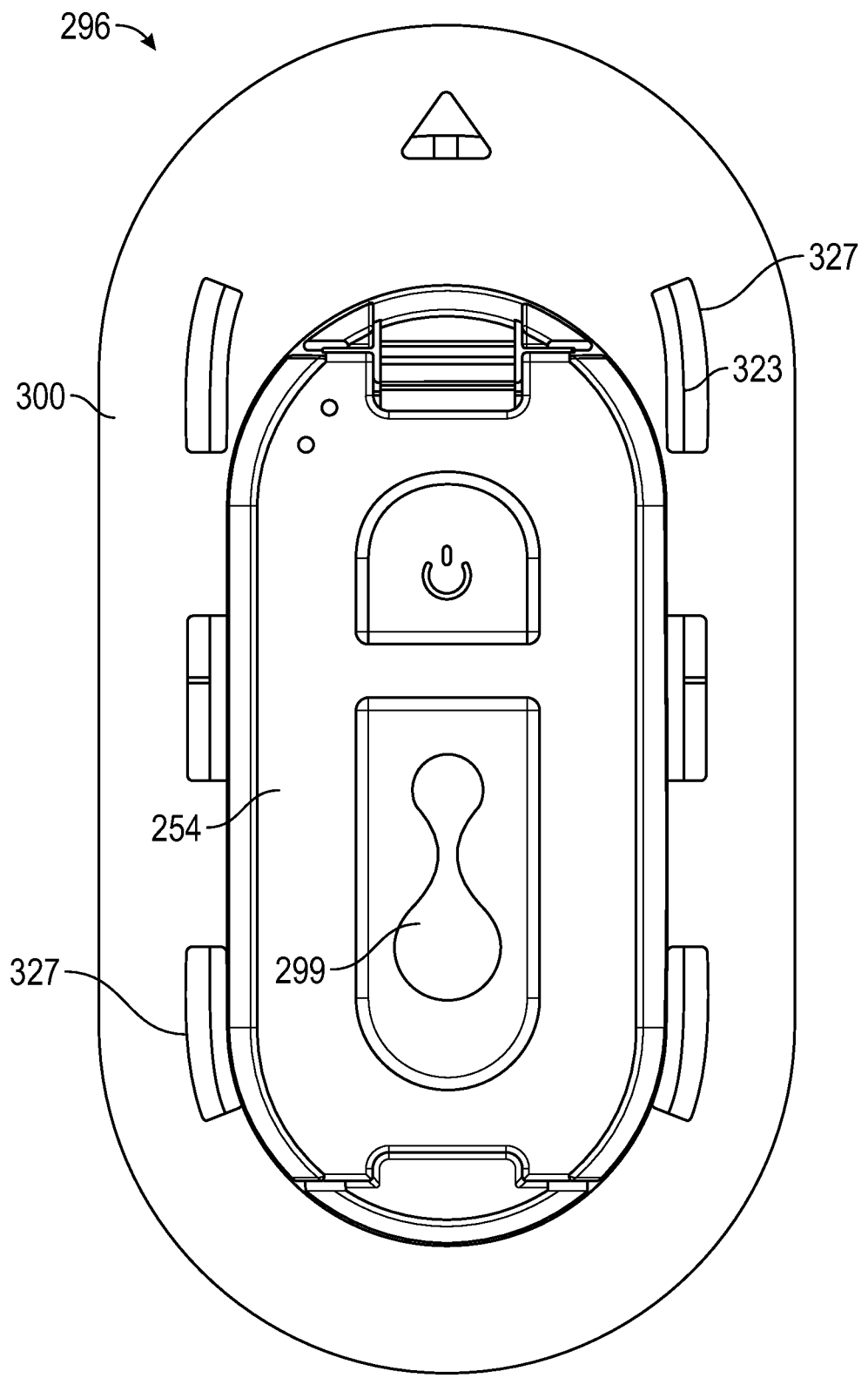
FIG. 23A is a top plan view of the flexible fluid capture substrate illustrated in FIG. 23 shown assembled, with the alternate embodiment of the wearable biofluidic volume and composition system illustrated in FIG. 22.

Referring now to FIGS. 23 and 23A, a third embodiment of the continuous wearable biofluid volume and composition system is shown assembled at 296 in FIG. 23A. A fourth embodiment of the flexible fluid capture substrate is shown exploded at 300 in FIG. 23. The continuous wearable biofluid volume and composition system 296 includes the flexible fluid capture substrate 300 and an electronic module 254.

The flexible fluid capture substrate 300 is similar to the flexible fluid capture substrates 120 and is also configured to be worn on a human body. The flexible fluid capture substrate 30 includes a flexible substrate body 302 having a first, outwardly facing surface 304, a second, skin-facing surface (not shown), and one or more sweat collection or microfluidic channels 306 formed in the flexible substrate body 302. Each microfluidic channel 306 has a first end defining a sweat inlet port 308, and a second end defining a sweat outlet port 310. The skin-facing surface (not shown) includes an adhesive, such as the patterned or striated adhesive 312, that bonds to skin of the wearer, and may be covered by a removable adhesive liner 314 formed from any desired flexible and air/oxygen impermeable material. The striated adhesive 312 also defines fluidic channels that prevent sweat from building up underneath the flexible fluid capture substrate 300, and also includes an opening 316 having a diameter larger than a diameter of the sweat inlet port 308, and configured to allow sweat to pool or accumulate on the skin and to be forced into the sweat inlet port 308.

Electrodes 318 and one or more electrical traces 320 may be printed on either side of a first flexible substrate layer 322, formed from a desired flexible material, including but not limited to silicone, clear polyester, PET, and TPU, as described in detail above. The flexible substrate layer 322 includes an electrical connector pad 324, similar to the electrical connector pad 180, configured to contact electrical connection pins, such as the pins 184 in the electronic module 182, a portion of which is shown in FIG. 12, and is attached to the skin facing side of the flexible substrate body 302. A second flexible substrate 323 may be attached to the outwardly facing surface 304 of the flexible substrate body 302.

The flexible fluid capture substrate 300 also includes an upper layer defining a skirt 326. The skirt 326 is formed from a flexible, soft material that may be softer and larger than the flexible substrate body 302 and the flexible substrate layer 322, such that peripheral edges of the skirt 326 extend outwardly beyond a peripheral edge of the flexible substrate body 302 and therefore contacts the skin of the wearer. The portion of the skirt 326 that contacts the skin of the wearer may also include an adhesive and thus adheres to skin. The skirt 326 provides a mechanical transition between the mechanical modulus of skin and the modulus of a flexible fluid capture substrate sub-assembly 300A that includes the fluidic substrate body 302, first flexible substrate layer 322, second flexible substrate layer 323, and the striated adhesive 312. By smoothing the transition between the modulus of skin and modulus of the flexible fluid capture substrate sub-assembly 300A, the peripheral edges of the flexible fluid capture substrate sub-assembly 300A are better adhered to the skin. The portion of the skirt 326 that contacts the skin, i.e., the peripheral edges of the skirt 326 extend outwardly beyond a peripheral edge of the flexible substrate body 302, also include a plurality of vent holes 327. The vent holes allow fluid, such as sweat, that is not captured in the microfluidic channel 306 to exit from between the flexible fluid capture substrate sub-assembly 300A and the skin to which it is adhered. As described above, the skirt 326 may be formed from any desired flexible, soft material, such as medical or kinesiology tape.

Referring to FIG. 23, in some embodiments of the flexible fluid capture substrate 322 a known resistor may be formed from the traces 328. Different fluidic substrate designs would have different resistor values. For example, a flexible fluid capture substrate that included a specific assay may have a resistor value of 500 ohms, but the same flexible fluid capture substrate without the specific assay would have a different resistor value, such as for example 100 ohms. This impedance can be measured by the electronic module 12 and mapped to a set of known flexible fluid capture substrate impedances to allow software in the electronic module 12 to determine the capability and/or feature set of the flexible fluid capture substrate 300A.

In the illustrated embodiment, the electronic module 254 includes a button 299 operative to allow the user to deactivate an alarm/alert/notification. Such alarms may include tactile alarms, such as vibration, sound or other audible acoustic signals, visual alarms, including lights, such as flashing lights, and/or text or other visual notifications on a smart device display screen, based on the electronic module 254 computing that a measurement taken exceeds a predetermined threshold including, but not limited to, the amount of sweat lost as an absolute amount, or as a percentage, of body mass, an environmental condition such as temperature, the duration of activity at metabolic rates, and/or for any other communicative function. The illustrated button 299 is designed to be large enough that it is relatively easy to push, including through any PPE that may be worn.

Figure 26A:
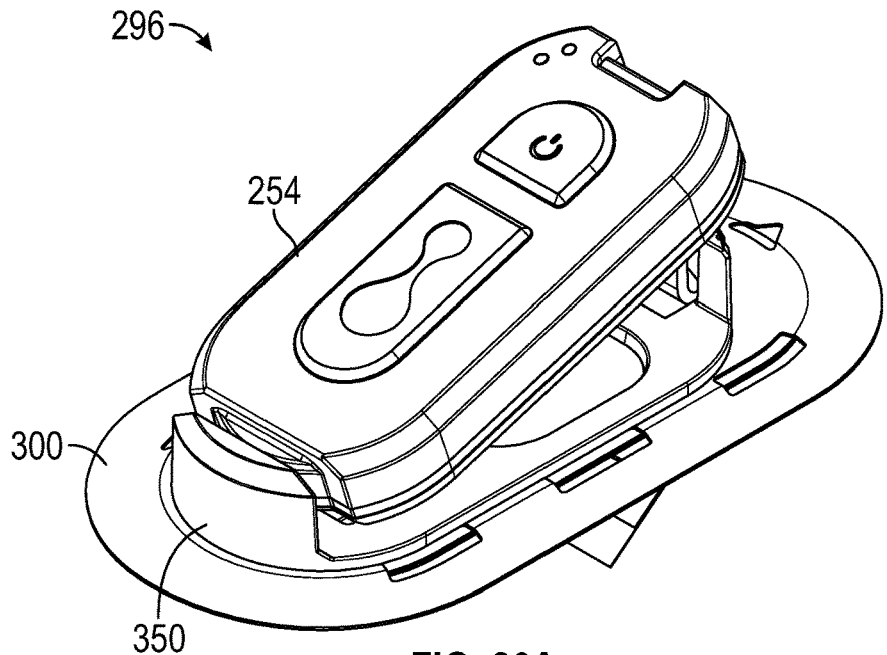
FIG. 26A is a perspective view of an alternate embodiment of the wearable biofluid volume and composition system illustrated in FIG. 23 showing the latch formed on the flexible fluid capture substrate.
Figure 26B:
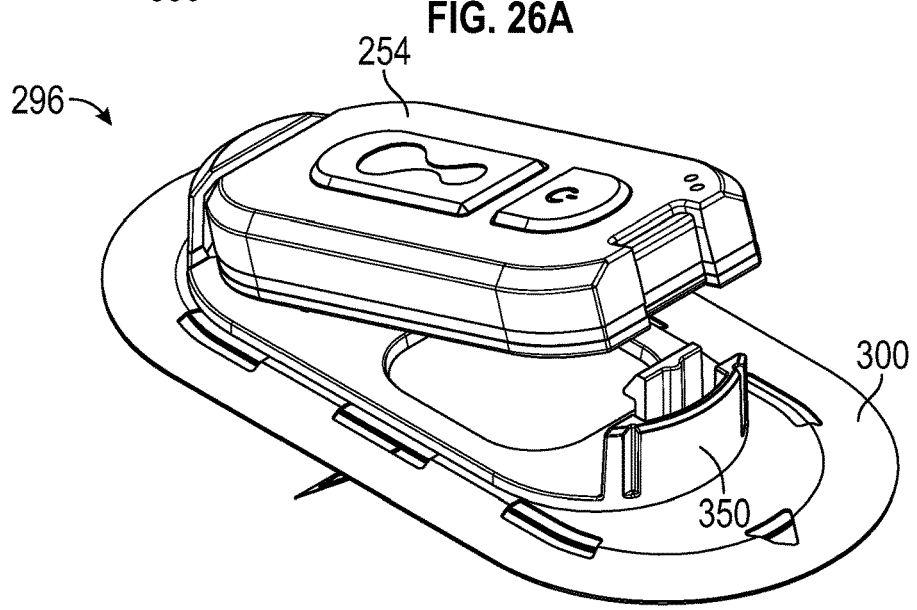
FIG. 26B is an alternate perspective view of the wearable biofluid volume and composition system illustrated in FIG. 26A.
Figure 26C:
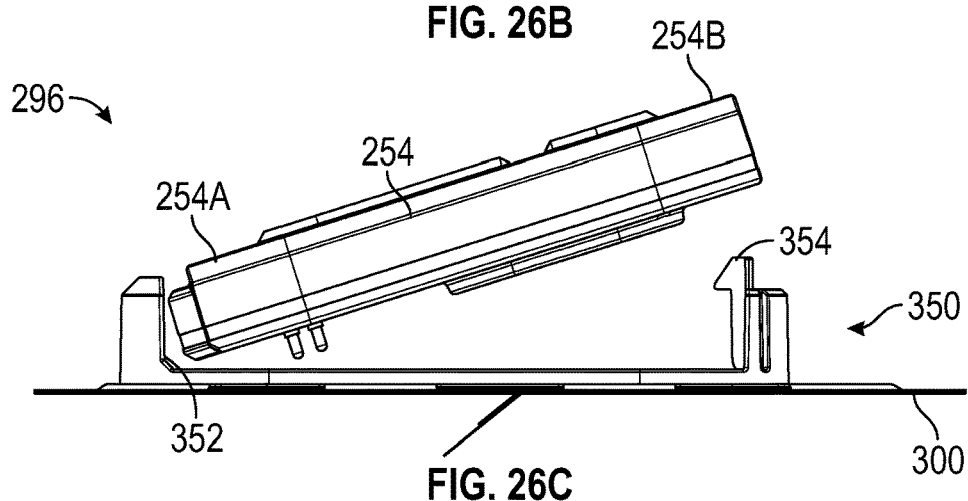
FIG. 26C is a side elevational view of the wearable biofluid volume and composition system illustrated in FIGS. 26A and 26B showing the electronic module being inserted into the latch.

Referring now to FIGS. 26A, 26B and 26C, the electronic module 254 of the continuous wearable biofluid and composition system 296 is secured to the flexible fluid capture substrate 300 by a 'drop-in' latch system 350. The latch system 350 allows electronic module 254 to be quickly and easily mounted to the flexible fluid capture substrate 300 with a one-handed operation. A first of toe end 254A of the electronic module 254 is inserted into a pocket 352 formed in the latch system 350. A second or top end 254B of the electronic module 254 is then pressed downwardly and locked into a clip portion 354 of the latch system 350.

In an alternate embodiment, text and graphic notifications may be displayed on a smartphone or other device and viewed when the user exceeds some threshold, or has not acknowledged performing a prescribed action such as rehydrating.

In an additional embodiment, text and graphic notifications and/or reports are delivered to the user when data streams such as weather from a weather report indicate that the user should be careful.

In a further embodiment, text and graphic notifications and/or reports are delivered to the user when the user's long-term behavior, including but not limited to a sweat loss profile, metabolic rate, and/or skin temperature, indicate a situation having increased risk for which action should be taken.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A wearable biofluid volume and composition system comprising:
   a microfluidic flexible fluid capture substrate having a microfluidic channel configured as a sweat collection channel, and configured to be worn on a human body and to collect and sense biofluid, the microfluidic flexible fluid capture substrate further having a plurality of conductive traces and electrodes; and an electronic module configured to measure and analyze data from the biofluid collected by the microfluidic flexible fluid capture substrate and to transmit the analyzed data to a smart device;

wherein the microfluidic flexible fluid capture substrate includes a flexible substrate body having a first, outwardly facing surface, a second, skin-facing surface, and a striated adhesive is on the skin-facing surface thereof that bonds to skin of a wearer, the striated adhesive defining fluidic channels that prevent sweat from building up underneath the microfluidic flexible fluid capture substrate.

2. The wearable biofluid volume and composition system according to claim 1, wherein the electronic module includes an electronic circuit therein configured to measure a volume of biofluid in the physiological range from about 1 μL to about 130 μL, and measure a sweat conductivity associated with a quantity of sodium in the physiological range from about 1 mg to about 5 g.

3. The wearable biofluid volume and composition system according to claim 1, wherein the electronic module is configured to analyze sweat loss and/or component sweat biomarkers in a wearer of the wearable biofluid volume and composition system, and provide real-time alerts and wirelessly transmit the analyzed sweat loss data the smart device, and wherein the real-time alerts are one of vibration, sound, audible acoustic signals, lights, and text or other visual notification on a smart device display screen.

4. The wearable biofluid volume and composition system according to claim 3, wherein the visual notification on the smart device display screen includes text and graphic notifications, wherein the visual notification is provided when the wearer one of exceeds a predetermined biometric threshold and fails to acknowledge rehydrating.

5. The wearable biofluid volume and composition system according to claim 3, wherein the visual notification on the smart device display screen includes weather data from a weather report that indicates that the wearer should be careful.

6. The wearable biofluid volume and composition system according to claim 3, wherein the visual notification on the smart device display screen includes a notification to take action due to increased risk when the wearer's long-term behavior exceeds a pre-determined threshold for one of sweat loss, metabolic rate, and skin temperature.

7. The wearable biofluid volume and composition system according to claim 3, wherein the component sweat biomarkers include electrolytes.

8. The wearable biofluid volume and composition system according to claim 1, wherein the smart device is one of a smartphone, a computer, a smart watch, and a networked central hub.

9. The wearable biofluid volume and composition system according to claim 1, wherein the conductive traces and electrodes are in contact with the sweat collection channel, and wherein electrodes contain one of an immuno-assay, an enzymatic assay, and an aptamer-based assay that create a voltage due to an electrochemical reaction with the biofluid.

10. The wearable biofluid volume and composition system according to claim 1, wherein the traces and electrodes are arranged in the form of a zipper along an axis of the sweat collection channel, such that traces on opposite sides of the sweat collection channel are parallel with each other and with the sweat collection channel, wherein the electrodes extend perpendicularly from the traces alternatingly crossing the sweat collection channel and forming the teeth of the zipper, and wherein the electrodes that extend across the sweat collection channel are in electrical contact with sweat in the sweat collection channel.

11. The wearable biofluid volume and composition system according to claim 1, wherein an exposed electrode is coated with a material that causes the electrode to be non-polarized and have a low junction potential.

12. The wearable biofluid volume and composition system according to claim 11, wherein the exposed electrode is coated with Ag/AgCl.

13. The wearable biofluid volume and composition system according to claim 1, wherein the microfluidic flexible fluid capture substrate includes a plurality of pairs of electrodes along a path of the microfluidic channel, wherein successive ones of the plurality of pairs of electrodes can electrically demarcate discrete, successive fill volume of the microfluidic flexible fluid capture substrate, and wherein the electronic module and the microfluidic flexible fluid capture substrate perform a method cooperatively to measure the impedance values from excitation and sensing of each of successive electrode pairs or a region along the microfluidic channel within the microfluidic flexible fluid capture substrate and resolve changes in volume, and compile all the impedance data from all the electrode regions along the microfluidic channel to obtain a total volume measurement.

14. The wearable biofluid volume and composition system according to claim 13, wherein the microfluidic flexible fluid capture substrate includes one of a plurality of the microfluidic channels, a fluid reservoir, and a combination of the plurality of the microfluidic channels and the fluid reservoir.

15. The wearable biofluid volume and composition system according to claim 1, wherein the microfluidic flexible fluid capture substrate includes the configuration and sizing of the electrode pad area and fluidic channel to allow for mass-production misalignment tolerance without reducing electrical performance, wherein the electronic module is connected to multiple pairs of the electrodes via one of multiplexing and simultaneous signal conditioning, and wherein the microfluidic flexible fluid capture substrate contains sets of electrodes that are localized to regions along the fluidic channel such that they measure only that region through one of multiplexing and simultaneous sampling.

16. The wearable biofluid volume and composition system according to claim 1, wherein the microfluidic flexible fluid capture substrate includes one or more traces with a defined impedance that can be measured by the electronic module to identify the type of microfluidic flexible fluid capture substrate.

17. The wearable biofluid volume and composition system according to claim 1, wherein the traces and electrodes are formed in an array and are arranged in Cartesian coordinate axes such that the array is configured to measure one of moisture and fluid along x and y axes.

18. The wearable biofluid volume and composition system according to claim 1, wherein the traces and electrodes are formed in an array and are arranged in polar coordinate axes with concentric rings such that the array is configured to measure biofluid as the biofluid spreads from a center outward in successive rings of the polar coordinate axes.

19. The wearable biofluid volume and composition system according to claim 1, wherein the electronic module is configured to measure one or more of:

voltages and currents generated by electrochemical reactions that occur on the microfluidic flexible fluid capture substrate;
biomarker characteristics over time to provide temporal data;
biomarker characteristics and temperature to calibrate volume fill;
biomarker characteristics and motion data to reject volume measurement fluctuation and to provide biomarker and fluid volume recommendations;
biomarker characteristics, temperature, and motion data to calculate sweat loss and metabolic rate to compute sustained heat exposure; and
motion values that have been correlated to one of a work task activity and an athletic activity workload, wherein the motion values are used as inputs in a rehydration recommendation algorithm and a re-hydration alert warning algorithm.

20. The wearable biofluid volume and composition system according to claim 1, wherein the electronic module includes an alarm configured to alert the wearer to perform a task.

21. The wearable biofluid volume and composition system according to claim 1, wherein the microfluidic flexible fluid capture substrate includes a ribbon cable extending outwardly therefrom, formed from the same material as the microfluidic flexible fluid capture substrate, and configured to be electrically connected to the electronic module.

22. The wearable biofluid volume and composition system according to claim 1, wherein the electronic module includes a spring-loaded connector that extends outwardly therefrom and is configured to make contact with printed conductive pads on the microfluidic flexible fluid capture substrate, and to be electrically connected to the electronic module, and wherein the electrical contact is maintained by the module being mechanically secured to the microfluidic flexible fluid capture substrate via a physical latch, enabling a user to attach the module to the fluidic microfluidic flexible fluid capture substrate with one hand.

23. The wearable biofluid volume and composition system according to claim 1, wherein the wearable biofluid volume and composition system is wirelessly connected to smart fitness equipment, and configured to download real-time data to the smart fitness equipment.

24. The wearable biofluid volume and composition system according to claim 1, wherein sweat data that is measured, logged, and analyzed by the wearable biofluid volume and composition system is wirelessly transmitted to a health management database, and wherein the receiving health management database is configured to allow the wearer to view and track one or more of the wearer's hydration, nutrition, and dietary needs before, during, and after physical activity.

25. The wearable biofluid volume and composition system according to claim 1, wherein sweat data that is measured, logged, and analyzed by the wearable biofluid volume and composition system is wirelessly transmitted to a health management database, and wherein the receiving health management database is configured to prepare incident reports in accordance with at least one of local, national, and industry safety regulations.

26. The wearable biofluid volume and composition system according to claim 1, wherein the analyzed data transmitted to the smart device is from multiple participants in a fitness activity, wherein the smart device assesses one of an average and weighted sweat rate for the participants in the fitness activity, wherein the one of the average and the weighted sweat rate is provided for use by potential participant in the fitness activity, and wherein the one of the average and the weighted sweat rate provided is indicative of an expected sweat rate for the potential participant to aid the potential participant in selecting classes based on sweat rate.

27. The wearable biofluid volume and composition system according to claim 1, wherein the microfluidic flexible fluid capture substrate further includes a fluid reservoir.

28. The wearable biofluid volume and composition system according to claim 1, wherein the microfluidic flexible fluid capture substrate further includes an outer layer opposite a surface of the microfluidic flexible fluid capture substrate that is adhered to the human body, wherein the outer layer defines a skirt that is formed from a flexible, soft material that is larger than the microfluidic flexible fluid capture substrate such that peripheral edges of the skirt extend outwardly beyond a peripheral edge of the microfluidic flexible fluid capture substrate, contact the skin, and have a plurality of vent holes formed therein, wherein the vent holes allow biofluid that is not captured in the microfluidic channel to exit from between the microfluidic flexible fluid capture substrate and the skin to which it is adhered.

29. The wearable biofluid volume and composition system according to claim 1, wherein the electronic module includes an on-board button operative to allow a user to deactivate an alarm, wherein the alarm is determined by the amount of sweat loss and/or hydration deficit defined by the amount of sweat loss minus the amount of water and electrolytes consumed, and wherein the deficit may be adjusted by data entry via one of the smartphone app, by pressing the on-board button on the electronic module, and via a connected smart water bottle configured to determine the amount of fluid consumed wirelessly to the wearable biofluid volume and composition system.

30. The wearable biofluid volume and composition system according to claim 1, wherein the electronic module includes a temperature sensor therein and an electrical connector extending outwardly therefrom, wherein the microfluidic flexible fluid capture substrate includes an electrical connector pad configured to contact the electrical connector, wherein a thermally conductive trace extends between the electrical connector and the temperature sensor, wherein the electrical connector is configured to function as a thermal conduit from the skin of a wearer to the temperature sensor, wherein the thermally conductive trace provides a high thermal conductivity path to the temperature sensor, and wherein active electrical components within the electronic module that generate heat are spaced a distance away from the temperature sensor and are insulated from the temperature sensor by a space defining a conductive moat.

31. A wearable biofluid volume and composition system comprising:
a microfluidic flexible fluid capture substrate configured to be worn on a human body, the microfluidic flexible fluid capture substrate including:
a flexible substrate body having a first, outwardly facing surface, a second, skin-facing surface, and a sweat collection channel formed therein, wherein the sweat collection channel has a first end defining a sweat inlet port, and a second end defining a sweat outlet port, a striated adhesive on the skin-facing surface thereof that bonds to skin of a wearer, the striated adhesive defining fluidic channels that prevent sweat from building up underneath the microfluidic flexible fluid capture substrate and further defining an opening having a diameter larger than a diameter of the sweat inlet port, the opening configured to allow sweat to accumulate on the skin and to be forced into the sweat inlet port, and a removable adhesive liner covering the striated adhesive;

a first flexible substrate layer having electrical traces, electrodes, and an electrical connector pad printed thereon, and attached to a surface of the flexible substrate body;

a second flexible substrate attached to a surface of the flexible substrate body opposite the first flexible substrate layer; and an upper layer defining a skirt, the skirt formed from a flexible, soft material that is softer and larger than the flexible substrate body, such that peripheral edges of the skirt extend outwardly beyond a peripheral edge of the flexible substrate body and contact the skin of the wearer, wherein the portion of the skirt that contacts the skin of the wearer includes an adhesive to adhere to skin, wherein the skirt provides a mechanical transition between a mechanical modulus of the skin to which it is adhered and a modulus of the flexible fluid capture substrate, and wherein the portion of the skirt that contacts the skin includes a plurality of vent holes configured to allow sweat that is not captured in the sweat collection channel to exit from between the flexible fluid capture substrate and the skin to which it is adhered;

an electronic module configured to measure and analyze data from the sweat collected by the microfluidic flexible fluid capture substrate and to transmit the analyzed data to a smart device, the electronic module including:

a base;

a cover;

a PCB assembly mounted therein, the PCB assembly including a PCB, a microcontroller, a plurality of functional electronic components mounted to the PCB, and a plurality of electrical connection pins configured to contact the electrical connector pad of the microfluidic flexible fluid capture substrate; and a button operative to allow the wearer to deactivate an alarm; and a latch system configured receive and retain the electronic module to the microfluidic flexible fluid capture substrate.

\* \* \* \* \*

UNITED STATES PATENT AND TRADEMARK OFFICE
CERTIFICATE OF CORRECTION

PATENT NO. : 11,559,225 B1
APPLICATION NO. : 17/746407
DATED : January 24, 2023
INVENTOR(S) : Stephen P. Lee et al.

It is certified that error appears in the above-identified patent and that said Letters Patent is hereby corrected as shown below:

In the Claims

Column 25, Line 38, please correct:
"a user to attach the module to the fluidic microfluidic flexible"
To:
--a user to attach the module to the microfluidic flexible--

Signed and Sealed this
Seventh Day of March, 2023

Katherine Kelly Vidal
*Director of the United States Patent and Trademark Office*